United States Patent
Cherkaoui

(10) Patent No.: US 6,534,135 B1
(45) Date of Patent: Mar. 18, 2003

(54) PROCESS OF PREPARING DISCOTIC LIQUID CRYSTALLINE COMPOUNDS

(75) Inventor: Mohammed Cherkaoui, Allschwil (CH)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/646,191

(22) PCT Filed: Mar. 22, 1999

(86) PCT No.: PCT/EP99/01873

§ 371 (c)(1),
(2), (4) Date: Sep. 14, 2000

(87) PCT Pub. No.: WO99/48844

PCT Pub. Date: Sep. 30, 1999

(30) Foreign Application Priority Data

Mar. 24, 1998 (EP) ............................................. 98105278

(51) Int. Cl.[7] .................... C09K 19/38; C09K 19/32; C09K 19/34; G02F 1/13; C07D 221/06; C07C 25/18

(52) U.S. Cl. .............. 428/1.1; 252/299.61; 252/299.62; 546/101; 546/108; 568/634; 568/647; 570/183; 570/187

(58) Field of Search ....................... 252/299.62, 299.61; 546/101, 108; 570/183, 187; 568/634, 647; 428/1.1

(56) References Cited

FOREIGN PATENT DOCUMENTS

DE          43 07 049       9/1994

OTHER PUBLICATIONS

Borner R.C.: "A flexible and rational synthesis of substituded triphenylenes by palladium–catalysed cross–coupling of arylzinc halides" Journal of the Chemical Society, Chemical Communications., No. 7, —Apr. 7, 1994 pp. 845–846, XP002106484 Letchworth GB.

Cherkaoui M Z et al: "On the synthesis of hexamethoxyphenanthrenes: an efficient phenanthrene synthesis via intramolecular oxidative cyclization of 2,2'–dihydrazonyl-biphenyls" New J. Chem. (NJCHE5, 11440546); 1997; vol. 21 (11); pp. 1203–1210, XP002106486 Institut Makromolekulare Chemie, Univ. Freiburg;Freiburg; D–79104; Germany (DE).

Liepa A.J.: "An improved phenanthrene synthesis: a simple route to (+−)–tylophorine" Journal of the Chemical Society, Chemical Communications., No. 22, —Nov. 16, 1977 pp. 826–827, XP002106485 Letchworth GB cited in the application.

*Primary Examiner*—Shean C. Wu
(74) *Attorney, Agent, or Firm*—Millen, White, Zelano & Branigan, P.C.

(57) ABSTRACT

The invention relates to a process of preparing a discotic liquid crystalline compound by intramolecular oxidative cyclisation of a diaryl compound in an organic solvent in the presence of a strong acid, characterized in that an oxidative agent comprising a chrom(VI)oxide derivative is used, to discotic liquid crystalline compounds obtainable from said process, to liquid crystalline media, (co)polymers or polymer networks with columnar phases comprising said discotic liquid crystalline compounds, and to the use of said discotic liquid crystalline compounds, liquid crystalline media or liquid crystalline (co)polymers with columnar phases for liquid crystal displays, optical elements like polarizers, compensators or colour filters, chemical sensors, charge transport materials, optical storage media, nonlinear optics, decorative pigments, adhesive or synthetic resins with anisotropic mechanical properties.

31 Claims, 7 Drawing Sheets

PROCESS OF PREPARING DISCOTIC LIQUID CRYSTALLINE COMPOUNDS

The invention relates to a process of preparing a discotic liquid crystalline compound by intramolecular oxidative cyclisation of a diaryl compound in an organic solvent in the presence of a strong acid, characterized in that an oxidative agent comprising a chrom(VI)oxide derivative is used.

The invention further relates to discotic liquid crystalline compounds obtainable by the above process and to the use of said discotic liquid crystalline compounds in liquid crystalline media with columnar phases and in the preparation of liquid crystalline (co)polymers or polymer networks.

The invention also relates to liquid crystalline media and liquid crystalline (co)polymers comprising inventive discotic liquid crystalline compounds, and to the use of inventive discotic liquid crystalline compounds, liquid crystalline media or liquid crystalline polymers for liquid crystal displays, optical elements like polarizers, compensators or colour filters, chemical sensors, charge transport materials, optical storage media, nonlinear optics, decorative pigments, adhesives or synthetic resins with anisotropic mechanical properties.

DETAILED DESCRIPTION OF THE INVENTION

Figure 1A:
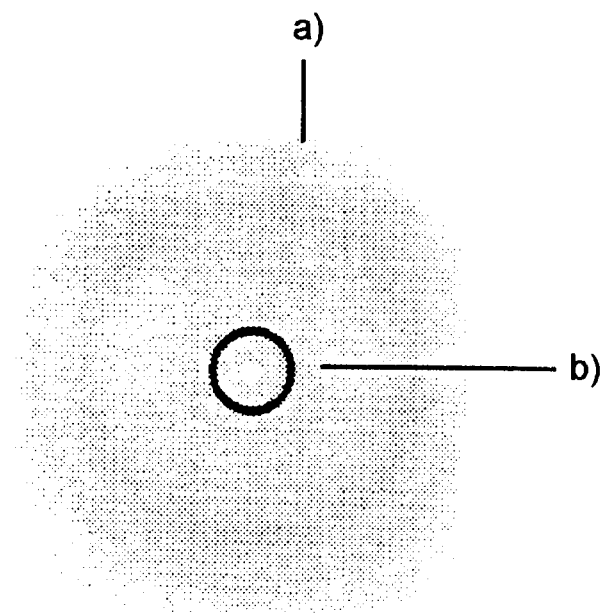
FIGS. 1A and 1B show the X-ray diffraction pattern of two samples of an inventive discotic liquid crystalline compound according to example 2.

Most of the liquid crystalline compounds and mixtures that are nowadays commercially used comprise calamitic, i.e. rod-shaped, moieties, whereas discotic, i.e. disk-shaped liquid crystalline compounds have hitherto found only limited applications.

Discotic liquid crystalline compounds exhibit columnar discotic or discotic nematic phases. Of these, especially the columnar phase has attracted commercial interest. In the columnar phase the disk-shaped molecules are stacked in columns that are laterally arranged in a two dimensional lattice. This leads to specific anisotropic properties of the columnar phase, such as e.g. anisotropic charge transport properties, which can be used in various applications.

Discotic liquid crystalline compounds, in particular discotic triphenylenes, have been proposed as charge transport and/or photosensitive materials for optical information storage, chemical sensors, photocopiers or laser printers (DE 43 39 711), light emitting diodes and electroluminescent displays (DE 43 43 412) or optically uniaxial negative compensation films (EP 0 646 829).

Most of the discotic liquid crystalline compounds described in prior art are triphenylene derivatives. Recently, however, it has been shown by G. Scherowsky and X. H. Chen, Liq Cryst. 17, 803 (1994) that phenanthrenes also exhibit columnar phases when being substituted by six aliphatic alkylcarbonyloxy chains. The DE 43 07 049 discloses hexaoctanoyloxyphenanthrenes that exhibit a columnar discotic phase.

On the other hand, hexaalkoxyphenanthrenes, which are also covered by the generic formula of the DE 43 07 049 but not specifically disclosed therein, have been reported by X. H. Chen, PhD thesis, TU Berlin (1994) to melt directly from the crystalline state to the isotropic state, without transiting via the columnar mesophase.

The phenanthrenes as disclosed in the DE 43 07 049 are prepared by photocyclisation of the corresponding stilbenes via irradiation with UV light. However, this method gives generally poor yields and is suitable only for synthesis at small scale.

A. J. Liepa and R. E. Summons, J. Chem. Soc. Chem. Comm. 826 (1977) reported the conversion of stilbenes into phenanthrenes by oxidative cyclisation in the presence of vanadium oxytrifluoride ($VOF_3$) in an acidic medium. However, besides other disadvantages this method is not suitable for large scale production, since the reagent $VOF_3$ is rather expensive.

Thus, there is still a demand for a method to synthesize discotic liquid crystalline compounds, in particular discotic phenanthrenes, that show a columnar discotic phase and can be obtained at large scale and in high yields.

The inventors have now found that discotic phenanthrene derivatives can be synthesized in high amounts by oxidative cyclisation of cyanostilbenes in an organic solvent in the presence of a pyridine complex of a chrom(VI)oxide derivative, in particular pyridinchlorochromate (PCC), and a strong acid, like e.g. boron trifluoride or trifluoroacetic acid. This method not only gives high yields, but is also suitable for large scale production.

Derivatives of chrom(VI)oxide and their organic complexes like e.g. chromic acid-pyridine complex, 2,2'-bipyridyl-chrom(VI)oxide complex, pyridinchloro- or fluorochromate (PCC, PFC) or pyridindichromate (PDC), are used in prior art in organic synthesis for the oxidative transformation from alcohols to aldehydes or ketones, as described e.g. in Houben-Weyl, Methoden der organischen Chemie Volume E3 ("Aldehydes"), Thieme-Verlag (Stuttgart). However, until now no example of intramolecular coupling between aromatic nuclei on using PCC has been reported in prior art.

One aim of the present invention is to provide discotic liquid crystalline compounds and methods for their preparation that do not bear the disadvantages of the compounds and methods of prior art as discussed above. Another aim of the present invention is to provide new polymerizable discotic liquid crystalline compounds and polymers, elastomers and polymer networks obtained from them. Another aim of the present invention is to extend the pool of discotic liquid crystalline materials available to the expert. Other aims of the invention are immediately evident to a person skilled in the art from the following description.

It has been found that the above mentioned aims can be achieved and the drawbacks of prior art can be overcome by providing discotic liquid crystalline compounds and a method to synthesize these compounds as described in this invention.

One object of the present invention is a process of preparing a discotic liquid crystalline compound by intramolecular oxidative cyclisation of a diaryl compound in an organic solvent in the presence of a strong acid, characterized in that an oxidative agent comprising a chrom(VI)oxide derivative is used.

Another object of the present invention is a process as described above of preparing a discotic liquid crystalline compound of formula I

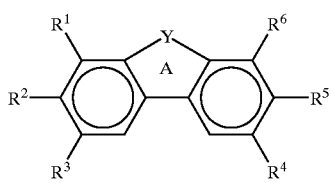

by intramolecular oxidative cyclisation of a diaryl compound of formula Ia

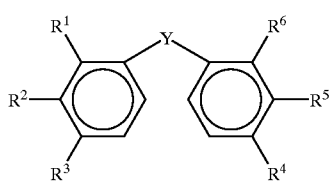

wherein

A is an aliphatic or aromatic five- or six-membered ring,
Y is —CH$_2$—, —NH—, —CH=CW—, —CO—, —COO—, or a radical >CH—CH< or >C=C< that is part of a mono- or bicyclic group comprising one or two condensated five- or six-membered aromatic or aliphatic rings, each of which may comprise one or more hetero atoms and may be unsubstituted, mono- or polysubstituted by $R^1$,
W is halogen, a dipolar group preferably selected from CN, NO$_2$, SO$_2$CH$_3$, SOCH$_3$, SOCF$_3$, SOOCH$_3$, SOOCF$_3$ or COR$^1$, or has one of the meanings of $R^1$,
$R^1$ to $R^6$ are in each case independently H, straight-chain or branched alkyl with 1 to 15 C atoms which may be unsubstituted, mono- or polysubstituted by halogen or CN, it being also possible for one or more non-adjacent CH$_2$ groups to be replaced, in each case independently from one another, by —O—, —S—, —NH—, —N(CH$_3$)—, —CH(OH)—, —CO—, —COO—, —OCO—, —OCO—O—, —S—CO—, —CO—S—, —CH=CH— or —C≡C— in such a manner that oxygen atoms are not linked directly to one another, or alternatively one or more of $R^1$ to $R^6$ are denoting P—(Sp—X)$_n$—,
P is a polymerizable group,
Sp is a spacer group having 1 to 15 C atoms,
X is group selected from —O—, —S—, —CO—, —COO—, —OCO—, —OCO—O—, —S—CO—, —CO—S— or a single bond, and
n is 0 or 1.

In a preferred embodiment of the present invention, the oxidative agent in the inventive process is a pyridinium complex or complex salt of a chrom(VI)oxide derivative, in particular pyridiniumchlorochromate (PCC).

In another preferred embodiment, boron trifluoride etherate or trifluoroacetic acid is used as strong acid in the inventive process.

A preferred embodiment of the present invention is a process of preparing a discotic liquid crystalline phenanthrene derivative of formula II

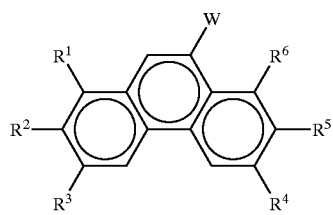

by intramolecular oxidative cyclisation of a stilbene derivative of formula IIa

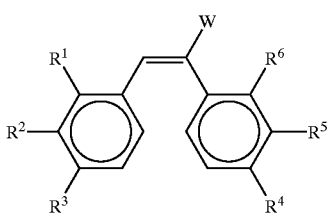

wherein W and $R^1$ to $R^6$ have each independently one of the meanings of formula I.

Further preferred embodiments relate to a process of preparing discotic liquid crystalline compounds of formula II, wherein W is —CN, —CHO or P—(Sp—X)$_n$,
at least two of $R^1$ to $R^6$ are each independently denoting straight-chain or branched alkoxy or alkenyloxy with 1 to 12 C atoms,
at least one of $R^1$ to $R^6$ is denoting P—(Sp—X)$_n$,
P is a vinyl, vinyloxy, acrylate, methacrylate, chloroacrylate, epoxy or styrene group.

Another preferred embodiment of the present invention is a process of preparing a discotic liquid crystalline phenanthrene derivative of formula II by reacting the benzaldehyde IIb*

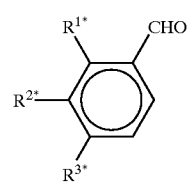

with the benzylcyanide IIc*

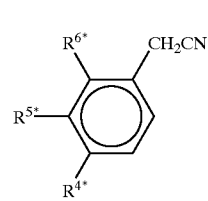

wherein $R^{1*}$ to $R^{6*}$ have one of the meanings of $R^1$ in formula I, in the presence of a base to the cyanostilbene IIa*,

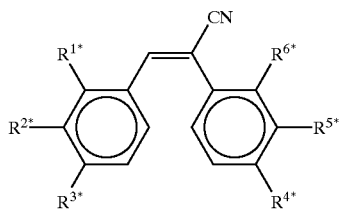

followed by intramolecular oxidative cyclisation of the cyanostilbene IIa* in an organic solvent in the presence of PCC and a strong acid to give the phenanthrene II*,

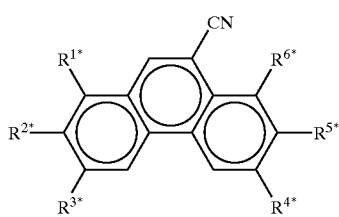

and optionally converting one or more of the groups $R^{1*}$ to $R^{6*}$ and/or the nitrile group of the phenanthrene II* by known methods into the desired substituents to give a phenanthrene derivative of formula II.

Particularly preferred is a process as described above wherein $R^{2*}$, $R^{3*}$, $R^{4*}$ and $R^{5*}$ are straight-chain or branched alkoxy or alkenyloxy with 1 to 12 C atoms.

Another object of the invention are discotic liquid crystalline compounds obtainable by a process as described in the foregoing and the following.

The formulae shown above and below embrace both known and new discotic liquid crystalline compounds. The new and preferred discotic liquid crystalline compounds as described above and below, in particular the new and preferred phenanthrene compounds, compounds of formula I and II and their subformulae, and polymerizable discotic compounds are another object of the present invention, independently of the method of their preparation.

Another object of the invention is the use of discotic liquid crystalline compounds prepared by the inventive process in liquid crystalline media with columnar phases and for the preparation of liquid crystalline (co)polymers, elastomers, polymer gels or polymer networks.

Further objects are liquid crystalline media with a columnar phase comprising at least two components, at least one of which is a discotic liquid crystalline compound as described in the foregoing and the following, and liquid crystalline polymers obtainable from discotic liquid crystalline compounds as described in the foregoing and the following by polymerization or polymeranaloguous reaction.

Yet another object of the invention is the use of inventive discotic liquid crystalline compounds, liquid crystalline media or liquid crystalline (co)polymers as described in the foregoing and the following for liquid crystal displays, optical elements like polarizers, compensators or colour filters, charge transport materials, optical storage media, nonlinear optics, decorative pigments, adhesives or synthetic resins with anisotropic mechanical properties.

Of the compounds of formula I and II especially preferred are those wherein W is CN, F, Cl, CHO or P—(Sp—X)$_n$—, in particular CN or CHO, very preferably CN. Further preferred are those wherein W is an alkyl group with 1 to 12 C atoms wherein at least one CH$_2$ group is replaced by —CO—.

Further preferred are compounds wherein at least one of the groups $R^1$ to $R^6$ is an achiral alkyl radical which is unsubstituted or substituted by at least one halogen atom, it being possible for one or two non—adjacent CH$_2$ groups of these radicals to be replaced by —O—, —S—, —CO—, O—CO—, —CO—O— or —O—CO—O— groups.

Halogen is preferably F or Cl.

If W or one or more of $R^1$ to $R^6$ are an alkyl or alkoxy radical, i.e. where the terminal CH$_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, methoxy, nonoxy, decoxy, undecoxy, dodecoxy, tridecoxy or tetradecoxy, for example.

Oxaalkyl, i.e. where one CH$_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 9-oxadecyl, for example.

A further preferred meaning for W and $R^1$ to $R^6$ is alkenyl, i.e. alkyl wherein one or more CH$_2$ groups are replaced by —CH=CH—. It is preferably straight chain or branched alkenyl with 2 to 7 C atoms. Straight chain alkenyl groups are preferred. Further preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl.

Of these, especially preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z,hexenyl, 4E-hexenyl, 4Z-heptenyl, 5-hexenyl and 6-heptenyl. Alkenyl groups with up to 5 C atoms are particularly preferred.

W and $R^1$ to $R^6$ may be achiral or chiral groups. In case of achiral groups they have preferably one of the preferred meanings given above. In case of chiral groups they are preferably selected according to the following formula IV:

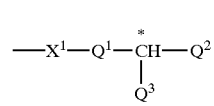

wherein $X^1$ has the meaning given for X, $Q^1$ is an alkylene or alkylene-oxy group with 1 to 10 C atoms or a single bond, $Q^2$ is an alkyl or alkoxy group with 1 to 10 C atoms which may be unsubstituted, mono- or polysubstituted by halogen or CN, it being also possible for one or more non-adjacent CH$_2$ groups to be replaced, in each case independently from one another, by —C≡C—, —O—, —S—, —NH—, —N(CH$_3$)—, —CO—, —COO—, —OCO—, —OCO—O—, —S—CO— or —CO—S— in such a manner that oxygen atoms are not linked directly to one another, or alternatively has the meaning given for P—Sp—, $Q^3$ is halogen, a cyano group or an alkyl or alkoxy group with 1 to 4 C atoms different from $Q^2$.

Preferred chiral groups are 2-butyl (=1-methylpropyl), 2-methylbutyl, 2-methylpentyl, 3-methylpentyl, 2-ethylhexyl, 2-propylpentyl, 2-octyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, for example.

In addition, compounds of the formula I and II wherein one or more of W and $R^1$ to $R^6$ are denoting an achiral branched group may occasionally be of importance as co-compounds, for example, due to a reduction in the tendency towards crystallization. Branched groups of this type generally do not contain more than one chain branch. Preferred achiral branched groups are isopropyl, isobutyl (=methylpropyl), isopentyl (=3-methylbutyl), isopropoxy, 2-methylpropoxy and 3-methylbutoxy.

Compounds of formula I and II are preferred wherein $R^6$ is H and $R^1$ to $R^5$ have one of the preferred meanings given above. Particularly preferred are compounds wherein one or more, preferably two to five, in particular four or five of the groups $R^1$ to $R^6$ are denoting straight-chain or branched alkoxy with 1 to 12, preferably 1 to 8 C atoms. Very particularly preferred are compounds wherein $R^6$ is H and $R^2$, $R^3$, $R^4$ and $R^5$ are alkoxy or alkenyloxy with 1 to 12, preferably 1 to 8 C atoms.

Further preferred are compounds wherein $R^1$ to $R^3$ and/or $R^4$ and $R^5$ respectively have the same meaning.

The polymerizable group P is preferably vinyl, vinyloxy, acrylate, methacrylate or epoxy group. Especially preferably P is vinyl, vinyloxy, acrylate or methacrylate, in particular vinyl or acrylate.

Particularly preferred are compounds of formula I and II comprising one polymerizable group. Further preferred are compounds having two to six, especially two to five, in particular two or three polymerizable groups. In particular preferred are compounds wherein W is cyano and one or more of $R^1$ to $R^6$ are carrying a polymerizable group.

As for the spacer group Sp all groups can be used that are known for this purpose to the skilled in the art. The spacer group Sp is preferably linked to the polymerizable group P by an ester or ether group or a single bond. The spacer group Sp is preferably a linear or branched alkylene group having 1 to 20 C atoms, in particular 1 to 12 C atoms, in which, in addition, one or more, non-adjacent $CH_2$ groups may be replaced by —O—, —S—, —NH—, —N($CH_3$)—, —CO—, —O—CO—, —S—CO—, —O—COO—, —CO—S—, —CO—O—, —CH(halogen)—, —CH(CN)—, —CH=CH— or —C≡C—.

Typical spacer groups Sp are for example —$(CH_2)_o$—, —$(CH_2CH_2O)_r$—$CH_2CH_2$—, —$CH_2CH_2$—S—$CH_2CH_2$— or —$CH_2CH_2$—NH—$CH_2CH_2$—, with o being an integer from 2 to 12 and r being an integer from 1 to 3.

Preferred spacer groups Sp are ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyl-iminoethylene and 1-methylalkylene, for example.

In a preferred embodiment of the invention the compounds of formula I and II comprise a spacer group Sp that is a chiral group of the formula V:

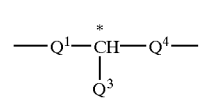

wherein $Q^1$ and $Q^3$ have the meanings given in formula IV, and
$Q^4$ is an alkylene or alkylene-oxy group with 1 to 10 C atoms or a single bond, being different from $Q^1$.

Further preferred chiral spacer groups are chiral groups based on naturally available materials, such as e.g. citronellol or lactate derivatives.

In particular preferred are polymerizable compounds wherein n is 1.

Another preferred embodiment relates to mixtures of polymerizable compounds wherein n is 0 and polymerizable compounds wherein n is 1.

In the event that one or more of the groups W and $R^1$ to $R^6$ are denoting P—Sp—X—, the spacer groups may be identical or different In the inventive process, derivatives of chrom(VI)oxide or their complexes or complex salts are used as oxidative agent. These reactants are known in the oxidation of alcohols to aldehydes or ketones, and are described e.g. in Houben-Weyl, Methoden der organischen Chemie, $4^{th}$ Edition, Volume E3 (Aldehydes), Page 290 ff (Thieme-Verlag, Stuttgart 1985).

The oxidative agent in the inventive process is preferably a complex of a chrom(VI)oxide derivative, such as chromic acid or halogeno-chromate, with an organic compound, like pyridine or 3,5-dimethylpyrazole, in particular a pyridine complex It is preferably selected from the group comprising chromic acid-pyridine complex, 2,2'-bipyridyl-chrom(VI) oxide complex, pyridinchloro- or fluorochromate (PCC, PFC) or pyridindichromate (PDC), and is particularly preferably PCC or PFC, very preferably PCC.

The intramolecular oxidative cyclisation according to the inventive process is carried out in an organic solvent. Polar solvents, like e.g. dichloromethane, chloroform or $CCl_4$, or non-polar solvents, like e.g. hydrocarbons such as petrolether or cyclohexane can be used. Preferably a polar solvent is used, in particular dichloromethane or chloroform.

The cyclisation reaction is carried out in the presence of a strong acid. Particularly preferred are strong lewis-acids, like e.g. boron trihalogenides and their complexes or per-halogenated organic acids, like e.g. perfluorocarboxylic acids. Particularly preferred are boron trifluoride etherate or trifluoroacetic acid, very preferably boron trifluoride etherate.

The temperature at which the cyclisation reaction is carried out is preferably within the range from −80° C. to +30° C., in particular from −30° C. to +25° C., very preferably from 0° C. to +20° C.

The selection of the optimum reaction conditions, such as the reaction parameters like e.g. the temperature or the components of the reaction mixture like e.g. the solvent and the acid, is also depending on the specific type of educts used. It is further depending on the other parameters of the reaction conditions and the individual components of the reaction mixture. Thus, the optimum conditions can be selected in each case independently by the expert from the preferred compounds and ranges mentioned above, in order to adapt them to the synthesis of the desired inventive compounds at high yields.

The discotic liquid crystalline compounds obtained by the inventive process can be further modified by transforming the substituents W, $R^1$ to $R^6$ and $R^{1*}$ to $R^{6*}$ to give the compounds of formula I and II.

It is further possible to introduce the desired substituents into the aromatic rings of the compounds of formula Ia, IIa and IIa* prior to the cyclisation reaction. This can be done e.g. by transforming the substituents $R^1$ to $R^6$ and $R^{1*}$ to $R^{6*}$ prior to or after the synthesis of the compounds of formula Ia, IIa and IIa* and/or by selecting these compounds or their educts accordingly.

For example, after the preparation of the cyanophenanthrene (II*) as described above and below it is possible to transform the cyano group by esterification or etherification into the desired substituent.

It is also possible to introduce one or more substituents with a terminal polymerizable group to the aromatic core prior to or after the cyclisation reaction. Thereby polymerizable compounds of formula I and II can be prepared. These can be used for the preparation of liquid crystalline polymers with columnar discotic phases.

The transformation or introduction of specific substituents as described above can be carried out by the expert without further elaboration by using known methods.

In the following, the inventive process is exemplarily described in detail for a particularly preferred embodiment, wherein a cyanostilbene of formula (IIa*) is prepared by reacting a substituted benzaldehyde of formula (IIb*) with a substituted benzyicyanide of formula (IIc*) in the presence of a base. The cyanostilbene (IIa*) is then converted into the phenanthrene (II*) by intramolecular oxidative cyclisation in an organic solvent with PCC as oxidative agent in the presence of a strong acid.

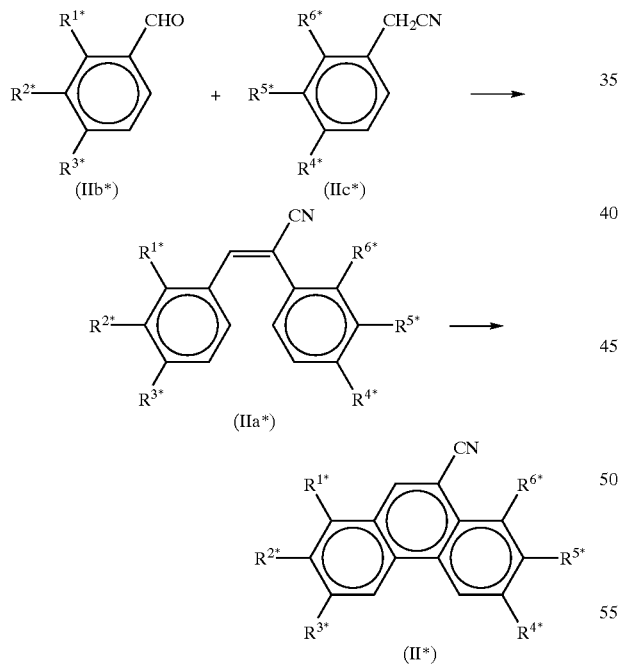

As mentioned above, the methods of preparation of discotic liquid crystalline phenanthrenes reported in prior art bear several disadvantages. Thus, the method described in the DE 43 07 049 via photocyclisation of the corresponding stilbenes by irradiation with UV light gives poor yields and is suitable only for synthesis at small scale.

The method reported by A. J. Liepa and R. E. Summons, J. Chem. Soc. Chem. Comm. 826 (1977) via oxidative cyclisation of stilbenes in the presence of $VOF_3$ in an acidic medium, although giving acceptable yields, is also not suitable for large scale production due to the use of the expensive reagent $VOF_3$.

In contrast to this, the synthesis of discotic liquid crystalline phenanthrenes according to the inventive method not only gives higher yields but is also suitable for large scale production.

Thus, PCC is about 10 to 20 times less expensive than $VOF_3$ and the oxidative cyclisation requires only two mole equivalents of PCC, while four mole equivalents of $VOF_3$ are needed.

In addition, it could be shown by the inventors for the preparation of hexamethoxyphenanthrenes that, when increasing the number of methoxy groups on the phenanthrene core, the yield of the oxidation reaction decreases strongly when $VOF_3$ is used, while still being high when PCC is used as oxidant.

This is a particular advantage of the inventive method, as it gives way to the synthesis of a broad variety of up to hexasubstituted phenanthrenes with still high yields. This is suitable for example when the liquid crystalline properties of the inventive compounds are optimized by changing the pattern of substitution of the aromatic rings, or when polymerizable compounds are prepared.

Another drawback of the method using $VOF_3$ is that the phenanthrenes undergo rapid decomposition in the acidic reaction medium when the reaction time, e.g. in an attempt to increase the yield, is prolonged by more than 10 to 15 minutes.

More specifically, the compounds of formula I and II can be prepared and their substituents be transformed according to or in analogy to the following reaction schemes.

Scheme 1

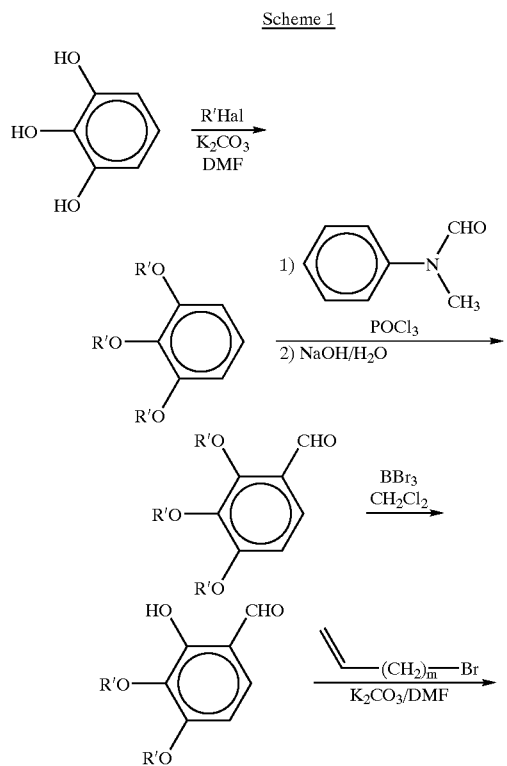

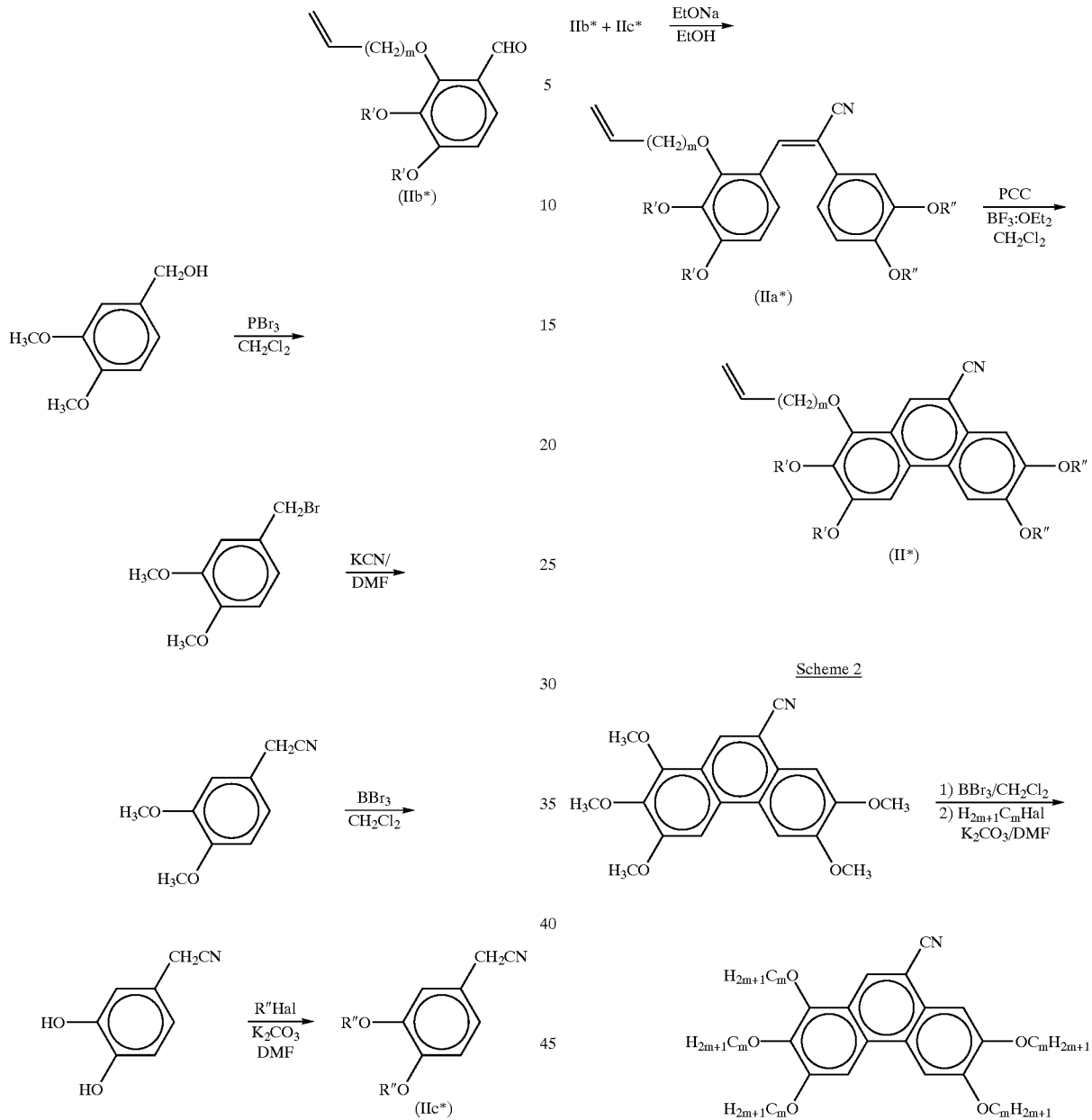
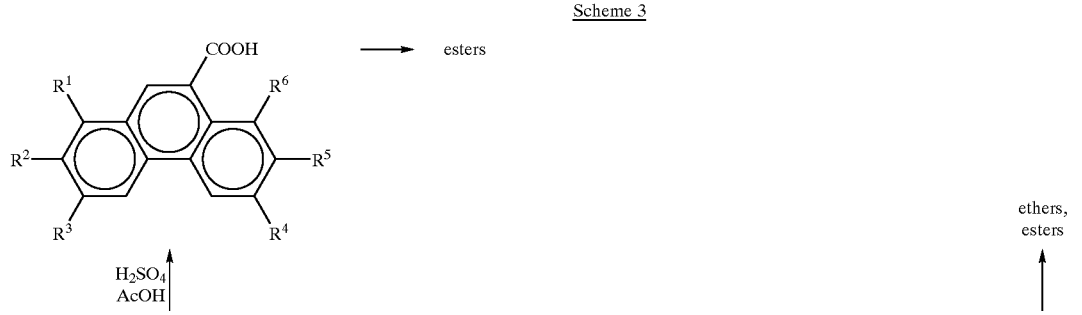
Scheme 3

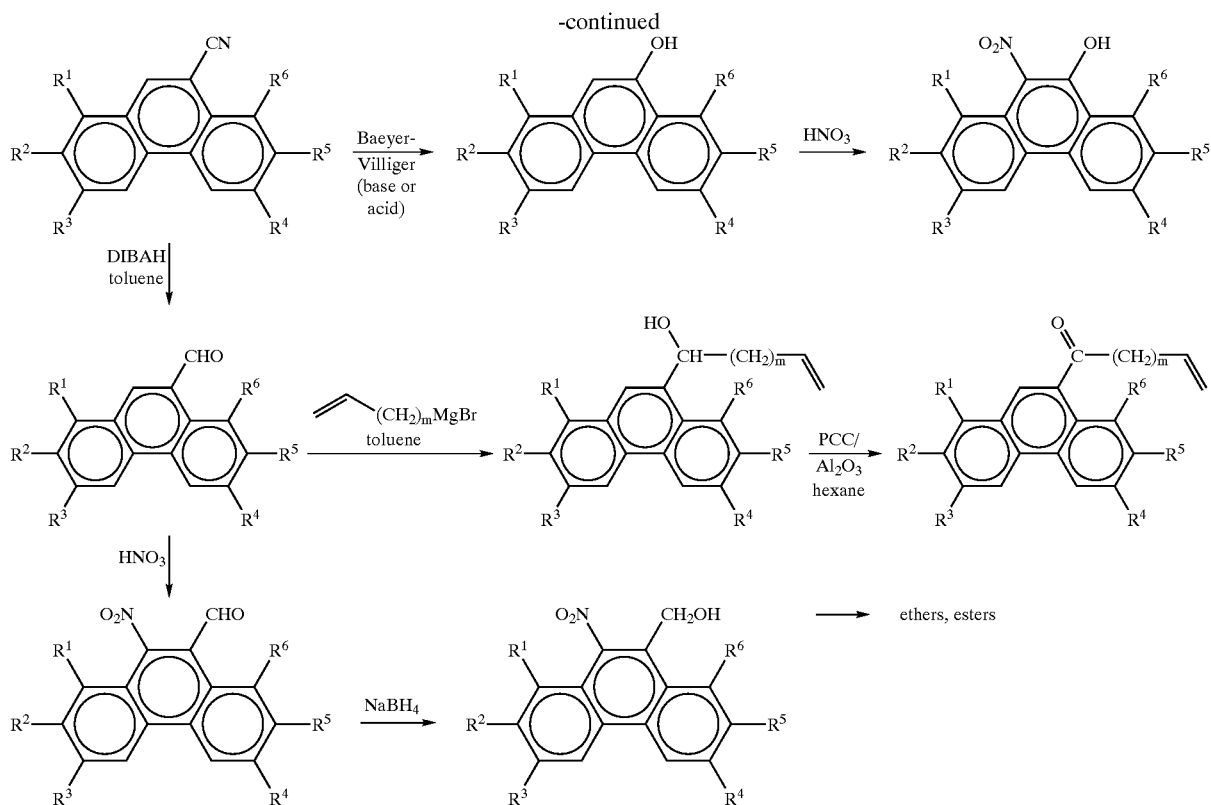

wherein R' and R" have one of the meanings of $R^1$ in formula I, $R^1$ to $R^6$ have the meaning of formula I, Hal is halogen and m is an integer from 1 to 12.

Further to the methods described above, the substituents R and $R^1$ to $R^6$ in the compounds of formula I and II can be converted into the desired groups prior to or after the cyclisation reaction by methods which are known per se and which are described, for example, in standard works of organic chemistry such as, for example, Houben-Weyl, Methoden der organischen Chemie, Thieme-Verlag, Stuttgart. Some specific methods of preparation can be taken from the examples.

Apart from the preparation of compounds of phenanthrenes of formula II as described above, it is also possible to prepare the following discotic compounds with the inventive process

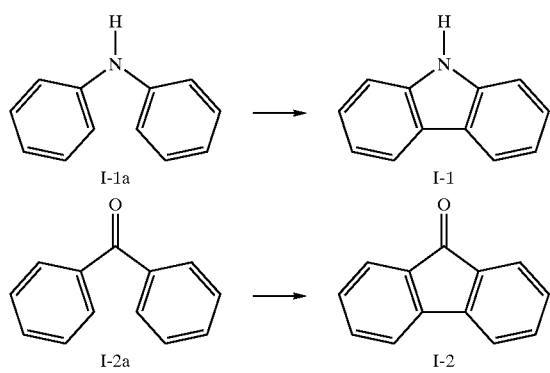

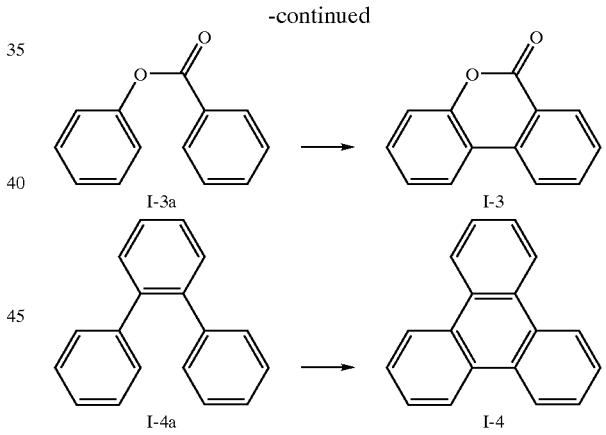

wherein the aromatic rings in the compounds I-1 to I-4 and I-1a to I-4a may also be mono- or polysubstituted by $R^1$ to $R^6$, and the central phenylene ring in compound I-4a and the corresponding ring in compound I-4 may also be connected via neighboured C atoms to another five- or six-membered aliphatic or aromatic ring which may also comprise one or more hetero atoms to form a condensated bicyclic system.

The skilled in the art can easily choose the specific reactants and conditions in order to adapt the inventive process as described for the preferred embodiments above to the synthesis of the compounds I-1 to I-4.

It is also possible to synthesize crosslinked polymers or polymer gels, e.g. by polymerization of mixtures comprising compounds of formula I and/or II in the presence of crosslinking agents, or by polymerization of mixtures comprising compounds of formula I and/or II wherein two or more of the radicals W and $R^1$ to $R^6$ are bearing a polymerizable group.

Depending on the content of compounds with more than one polymerizable group (multifunctional compounds) in the polymerizable mixture, the crosslink density is varied. When small amounts of multifunctional compounds are used, liquid crystalline elastomers are obtained, whereas in the presence of high amounts of multifunctional compounds liquid crystalline duromers are obtained.

In particular densely crosslinked polymers show very high thermal stability of the optical and mechanical properties compared to linear polymers.

Liquid crystalline polymers can be prepared from the inventive discotic compounds e.g. by radicalic, cationic or anionic polymerization of compounds of formula I or II wherein at least one of W and $R^1$ to $R^6$ is comprising a terminal vinyl, vinyloxy, acrylate, methacrylate, chloroacrylate, epoxy or styrene group.

Polymerization can be carried out e.g. by solution polymerization or by in-situ polymerization. Radicalic solution polymerization can be carried out for example in a solvent like dichloromethane, tetrahydrofuran or toluene using AIBN as an initiator and heating for 24 hours at 30 to 60° C.

In order to obtain polymers with macroscopic uniform orientation, the liquid crystalline polymers prepared by solution polymerization can be subsequently aligned e.g. by uniaxial shearing and/or by applying special means like electric or magnetic fields and high temperatures.

A particularly suitable method to prepare liquid crystalline polymers with uniform orientation is by in-situ polymerization of polymerizable inventive compounds or polymerizable mixtures comprising the inventive compounds in their liquid crystalline phase. In-situ polymerization can be carried out e.g. by irradiation of the polymerizable material with UV light in the presence of a UV-photoinitiator, like for example the commercially available Irgacure 651 (from Ciba Geigy AG).

According to this method, the polymerizable material is coated as a thin layer onto a substrate, aligned in its liquid crystalline phase by conventional techniques and cured by exposure to UV light to fix the alignment. A detailed description of this method can be found in D. J. Broer et al., Makromol.Chem. 190, 2255ff. and 3202ff. (1989).

In addition to light- or temperature-sensitive initiators the polymerizable mixture may also comprise one or more other suitable components such as, for example, crosslinking agents, catalysts, stabilizers, co-reacting monomers or surface-active compounds.

As substrates for example glass plates or plastic films can be used. To achieve uniform alignment, the films can be sheared for example by means of a doctor's blade. In some embodiments it may be of advantage to apply a second substrate in order to exclude water or oxygen that may inhibit the polymerization. Alternatively the curing can be carried out under an atmosphere of inert gas.

Another method to prepare liquid crystalline polymers from the inventive discotic compounds is by polymeranaloguous reaction. For example, compounds of formula I and II carrying terminal C—C-double bonds can be added to a polyhydrogensiloxane chain by hydrosilylation reaction in the presence of a catalyst, like e.g. the commercially available Pt catalyst SLM 86005 (from Wacker Chemie, Germany).

Crosslinked polymers, such as elastomers or densely crosslinked polymer networks can be obtained by the above hydrosilylation reaction of compounds of formula I and II comprising two or more substituents with a terminal double bond, or by using e.g. divinyl compounds as crosslinkers.

It is also possible to prepare liquid crystalline elastomers with a chemically permanent director alignment via a two-step crosslinking process as described e.g. by J. Küpfer, H. Finkelmann in Makromol.Chem.Rap.Comm.12, 717–726 (1991). According to this method, in a first crosslinking step a slightly crosslinked elastomer is prepared. This elastomer is subjected to uniaxial deformation as a result of which the director is macroscopically aligned in a uniform orientation. The uniform orientation is then permanently fixed by a second crosslinking step to give a liquid single crystal elastomer.

Polymer gels comprising linear or crosslinked polymers can be obtained e.g. from polymers comprising the inventive discotic compounds by mixing these polymers with low molecular weight liquid crystal (LMW-LC) compounds, or by polymerizing the inventive discotic compounds as described above and below in the presence of LMW-LC compounds. In particular, polymer gels can be prepared by in-situ polymerization of mixtures comprising inventive polymerizable discotic compounds and LMW-LC compounds.

The inventive discotic liquid crystalline compounds of formula I and II as well as liquid crystalline materials with columnar phases obtainable from or comprising these compounds, such as liquid crystalline media, liquid crystalline polymers, elastomers, polymer gels and polymer networks, can be used in various applications, like those mentioned above in the paragraphs discussing prior art.

For example, these materials are suitable for liquid crystal displays, optical elements like polarizers, compensators or colour filters, chemical sensors, charge transport materials, optical storage media, nonlinear optics, decorative pigments, adhesives or synthetic resins with anisotropic mechanical properties.

In particular, inventive compounds comprising polar groups, like CN or halogen, can be switched between different states in an electric field and are thus suitable for electrooptical applications.

Inventive compounds comprising one or more chiral groups can be used as chiral dopants, in ferroelectric media and in nonlinear optics.

Without further elaboration, it is believed that one skilled in the art can, using the preceding description, utilize the present invention to its fullest extent The following examples are, therefore, to be construed as merely illustrative and not limitative of the remainder of the disclosure in any way whatsoever.

In the foregoing and in the following examples, unless otherwise indicated, all temperatures are set forth uncorrected in degrees Celsius and all parts and percentages are by weight.

The mesophase behaviour of the compounds prepared in the following examples, unless otherwise indicated, has been investigated and the phase transition temperatures determined by polarization microscopy and/or differential scanning calorimetry (DSC).

The following abbreviations are used to illustrate the phase behaviour of the compounds: G=glassy; K=crystalline; D=columnar discotic; I=isotropic. The numbers between these symbols indicate the phase transition temperatures in degree Celsius. Numbers in brackets indicate a monotropic phase transition, i.e. a transition that is observed only upon cooling, unless otherwise indicated.

COMPARISON EXAMPLE

The efficiencies of PCC and $VOF_3$ as oxidative agent in the intramolecular cyclisation reaction of tetra-, penta- and hexamethoxycyanostilbenes have been compared experimentally. The synthesis of the cyanostilbenes is described below. The results are depicted in table 1.

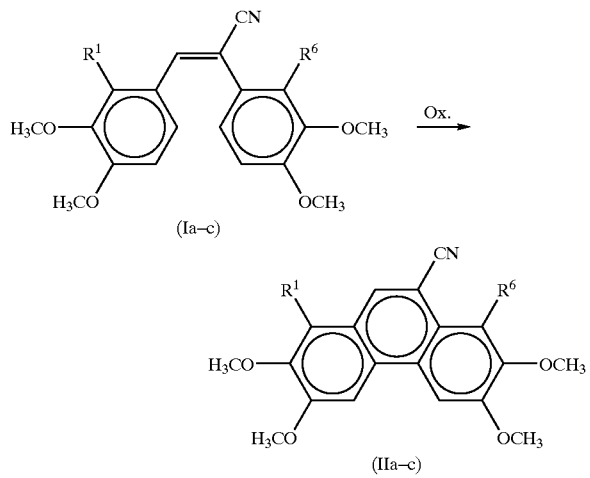

with $R^1$ and $R^6$ denoting H or $OCH_3$.
The compounds (Ia–c) have been prepared as follows:

Ia) 2,3-Bis-(3,4Dimethoxy-phenyl)-acrylonitrile
(Procedure A)

$(R^1=R^6=H)$

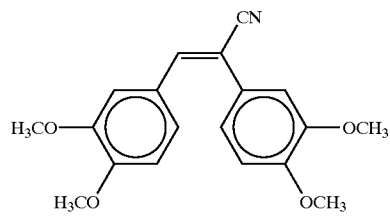

To a stirred solution of 3,4-dimethoxybenzaldehyde (1.66 g, 100 mmol) and 3,4-dimethoxyphenyl-acetonitrile (1.77 g, 10 mmol) in 50 ml of absolute ethanol, cooled at 0° C. and maintained under nitrogen atmosphere, sodium ethylate (30 mmol) was portionwise added (10 portions, 1 portion/2 min). After complete addition and stirring for further 6 h at room temperature the reaction mixture was cooled to 0° C. and a yellow precipitate occurs. This precipitate was filtered off, washed with ethanol (100 ml) and dried under reduced pressure. This afford the desired stilbene as yellow powder (yield 3 g, 92%).

Ib) 2-(3,4-Dimethoxy-phenyl)-3-(2,3,4-trimethoxy-phenyl)-acrylonitrile $(R^1=OCH_3, R^6=H)$

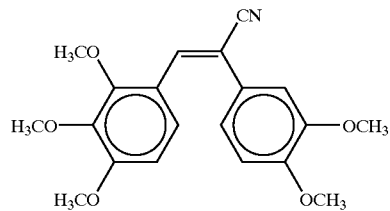

Following the Procedure A, the reaction was performed with 1.96 g of 2,3,4-trimethoxybenzaldehyde (10 mmol) and 1.77 g 3,4-dimethoxyphenyl-acetonitrile (10 mmol), affording 2-(3,4-dimethoxy-phenyl)-3-(2,3,4-trimethoxy-phenyl)-acrylonitrile as yellow powder (yield 3.2 g, 90%).

Ic) 2,3-Bis-(2,3,4-Trimethoxy-phenyl)-acrylonitrile $(R^1=R^6=OCH_3)$ 2,3,4-Trimethoxyphenyl-acetonitrile

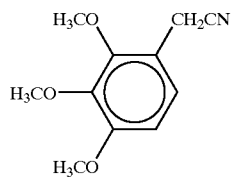

Phosphortribromide (6.83 g, 25.22 mmol) was added dropwise to a stirred solution of 2,3,4-trimethoxybenzyl alcohol (10 g, 54.44 mmol) in dichloromethane (100 ml), cooled at 0° C. After 30 min of vigorous stirring, the reaction mixture was slowly quenched with 100 g of ice-water. The dichloromethane layer was separated and the aqueous layer was further extracted with dichloromethane (2×100 ml). The combined extracts were twice washed with a saturated solution of sodium chloride (2×150 ml). The organic solution was dried over magnesium sulphate and evaporated to give 10 g (yield 76%) of the benzylbromide 2 as a colourless oil. As soon as isolated, the benzyl bromide compound was directly used for the next step. In fact the compound degradated after one night even at +4° C. The obtained 1-bromomethyl-2,3,4-trimethoxybenzene oil was treated with KCN (6.52 g, 100 mmol) in dry DMF (30 ml), at 0° C. and under nitrogen atmosphere. The obtained mixture was stirred for 3 g at 0° C. and 1 h at 60° C. The cooled reaction mixture was poured into water (80 ml) and extracted with diethylether (3×150 ml). The crude benzylcyanid was chromatographed on silica (diethylether/petroleumether: 1/3) to give 2,3,4-trimethoxyphenyl-acetonitrile as a white crystalline material (Yield: 6.8 g; 86%).

2,3-Bis-(2,3,4-trimethoxy-phenyl)-acrylonitrile

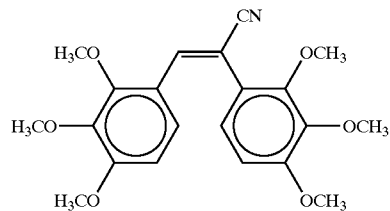

Following the Procedure A, the reaction was performed with 1.96 g of 2,3,4-trimethoxybenzaldehyde (10 mmol) and 2.07 g of 2,3,4-trimethoxyphenyl-acetonitrile (10 mmol), affording 2,3-bis-(2,3,4-trimethoxy-phenyl)-acrylonitrile as yellow powder (yield 3.6 g, 93%).

The transformation of the cyanostrilbenes (Ia–c) into the phenanthrenes (IIa–c) by oxidative cyclisation is described below with PCC as oxidative agent. The cyclisation of (Ia–c) with $VOF_3$ as oxidative agent was carried out in the same way, with the difference being that instead of PCC $VOF_3$ was added in a molar amount twice as much as that of PCC.

IIa) 2,3,6,7-Tetramethoxy-phenanthrene-9-carbonitrile (Procedure B)

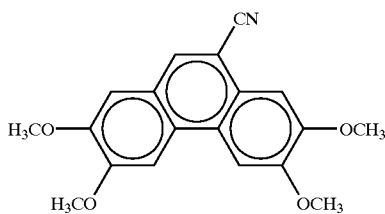

2,3-Bis-(3,4-dimethoxy-phenyl)-acrylonitile (1.83 g, 5.63 mmol) was dissolved in absolute dichloromethane (100 ml) and the obtained solution was cooled to 0° C. and maintained under nitrogen atmosphere. Boron trifluoride etherate (1.76 g, 12.39 mmol) was dropwise added (within 15 min) to the reaction mixture which was stirred for further 15 min at 0° C. At this temperature, pyridinium chlorochromate (PCC) (2.43 g, 11.26 mmol), was portionwise added (10 portions, 1 portion/min) to the reaction mixture which turned green-brown. After complete addition of PCC, the reaction mixture was stirred for further 10 min, poured into water (200 ml), and extracted with dichloromethane (2×200 ml). The combined organic extracts were dried over magnesium sulphate and evaporated under reduced pressure. The obtained brown residue was chromatographed on silica ($CH_2Cl_2$). This afford a yellow material which was further purified by crystallisation in ethanol/dichloromethane: 9/1 to give 2,3,6,7-tetramethoxy-phenanthrene-9-carbonitrile as white powder (yield 1.75 g, 96%).

IIb) 1,2,3,6,7-Pentamethoxy-phenanthrene-9-carbonitrile

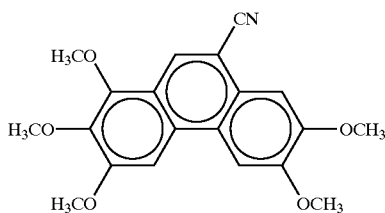

Following the Procedure B, the reaction was performed with 1.78 g of 2-(3,4-dimethoxy-phenyl)-3-(2,3,4-trimethoxy-phenyl)-acrylonitrile (5 mmol), boron trifluoride ehterate (1.56 g, 11 mmol) and PCC (2.15 g, 10 mmol), 1,2,3,6,7-pentamethoxy-phenanthrene-9-carbonitrile as white powder after crystallisation in EtOH/CH2Cl2:19/1 (yield 1.6 g, 90%).

IIc) 1,2,3,6,7,8-Hexanethoxy-phenanthrene-9-carbonitrile

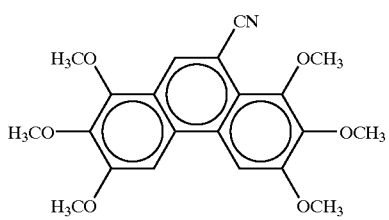

Following the Procedure B, the reaction was performed with 1.93 g of 2,3-Bis-(2,3,4-trimethoxy-phenal)-acrylonitrile (5 mmol), boron trifluoride etherate (1.56 g, 11 mmol) and PCC (2.15 g, 10 mmol), affording 1,2,3,6,7,8-hexamethoxy-phenanthrene-9-carbonitrile as white crystalline material after crystallisation in ethanol (yield 1.65 g, 87%).

Table 1 shows the results of the comparative experiment in which either PCC or $VOF_3$ were used as oxidative agent in the preparation of the phenanthrenes IIa–c.

TABLE 1

| No. | $R^1$ | $R^6$ | $VOF_3$ | PCC |
|---|---|---|---|---|
| IIa | H | H | 85% | 96% |
| IIb | $OCH_3$ | H | 50–55% | 90% |
| IIc | $OCH_3$ | $OCH_3$ | 32–54% | 87% |
| | reaction time | | 10–15 min < decomposition | 5 min < stability |

From table 1 it can easily be recognized that PCC is a more efficient oxidative agent than $VOF_3$, in particular when increasing the number of substituents on the aromatic rings of the cyanostilbenes Ia–c. It can also be seen that in the case of $VOF_3$ it is not possible to improve the yield by increasing the reaction time, since decomposition of the phenanthrene occurs.

EXAMPLE 1

1,2,3,6,7-Pentakis-heptyloxy-phenanthrene-9-carbonitrile (1) has been prepared as follows:

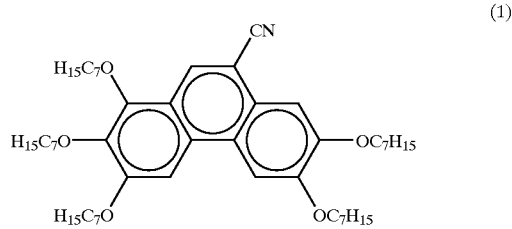

(1)

Under nitrogen atmosphere, a solution of 1,2,3,6,7-Pentamethoxy-phenanthrene-9-carbonitrile (0.75 g, 2.12 mmol) in $CH_2Cl_2$ (10 ml) was cooled to −76° C. and treated by a dropwise addition of 1M $CH_2Cl_2$ solution of $BBr_3$ (14 ml). After complete addition (15–20 min), the reaction mixture was stirred at room temperature for 30 min and heated at reflux during 12 h. After being cooled to 0° C. the reaction mixture was gently treated with 2 ml of methanol (dropwise addition), poured into 30 g of ice-water and stirred for further 20 min at room temperature. The obtained mixture was saturated with NaCl and extracted with diethylether (5×60 ml). The combined organic extracts were washed with 100 ml of saturated NaCl solution, dried over magnesium sulphate and evaporated under reduced pressure to afford the pentahydroxy-phenanthrene as slightly yellow crystalline material. It was then dissolved in dry DMF (5 ml) containing 2.40 g (10.60 mmol) of 1-iodo heptane. To this solution, maintained under nitrogen atmosphere and stirred at room temperature, potassium carbonate (1.46 g, 10.60 mmol) was added and the obtained mixture was stirred at 80° C. overnight. The cooled reaction mixture was gently poured into HCl 3N (30 ml) and extracted with diethylether (3×50 ml). The combined organic extracts were washed with 80 ml of saturated NaCl solution, dried over magnesium sulphate and evaporated under reduced pressure. The obtained oily residue was chromatographed on silica (dichloromethane/petroleumether: 1/1) to give 1,2,3,6,7-pentakis-heptyloxy-phenanthrene-9-carbonitrile as a white liquid-crystalline material (Yield: 0.84 g; 51%).

Compound (1) exhibits an enantiotropic columnar discotic phase and shows the phase behaviour K-28 D 66.8 I.

Figure 1B:
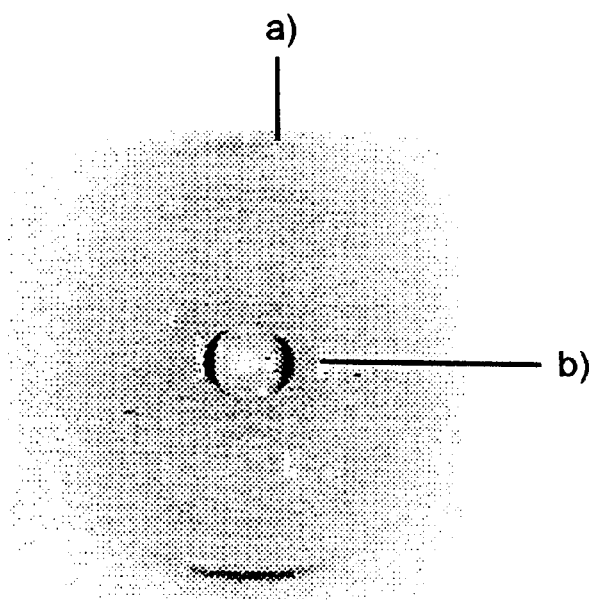

The columnar discotic phase of compound (1) was investigated by X-ray experiments. FIGS. 1A and 1B show the X-ray diffraction pattern of two samples of compound (1) in its columnar discotic phase at room temperature, with FIG. 1A relating to an unoriented sample that exhibits a polydomain structure, and FIG. 1B relating to a sample that exhibits a monodomain structure after it was sheared uniaxially.

The incident X-ray beam is perpendicular to the surface of the detector and to the shear direction, the latter of which is corresponding to the vertical of FIGS. 1A and 1B. In FIG. 1A and 1B two reflections are shown: The wide angle reflection (a) is attributed to the intracolumnar disk spacing while the small angle reflection (b) is due to the intermolecular disk spacing.

For the polydomain sample, the distribution of the liquid crystalline director is isotropic, corresponding to a homogeneous azimuthal distribution of the X-ray intensities as depicted in FIG. 1A.

For the sheared monodomain sample, the distribution of the director is anisotropic, corresponding to sharp maxima in the azimuthal distribution of the intensities as depicted in FIG. 1B. Of these, the wide angle reflection maxima (a) are perpendicular to the shear axis, whereas the small angle maxima (b) are parallel to the shear axis.

These results clearly demonstrate that the columns of the discotic phase in compound (1) can be oriented macroscopically parallel to the shear axis with a high quality of alignment.

The following compounds have been prepared analoguously

| R¹ | R² | R³ | R⁴ | R⁵ | Phase Behaviour |
|---|---|---|---|---|---|
| OC₄H₉ | OC₄H₉ | OC₄H₉ | OC₄H₉ | OC₄H₉ | K (30 D 77) 81 I |
| 2-MB | 2-MB | 2-MB | OC₇H₁₅ | OC₇H₁₅ | K 77 D 86.6 I |

2-MB = 2-methylbutyloxy

EXAMPLE 2a

The compound 6,7-Bis-heptyloxy-3,4-bis-[(S)-2-methyl-butoxy]-2-(pent-4-enyloxy)-phenanthrene-9-carbonitrile (2) carrying a polymerizable reactive group has been prepared as follows:

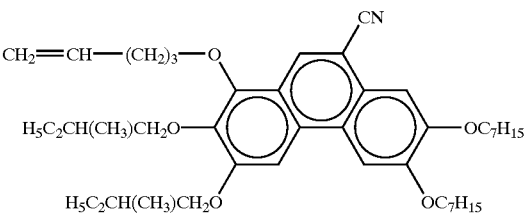

(2)

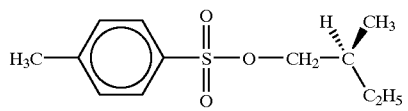

(S)-2-Methyl-butyl p-Toluenesulphonate

To a ice-cooled solution of p-toluenesulphonyl chloride (9.53 g, 50 mmol), (S)-2-methylbutan-1-ol (4.41 g, 50 mmol) in absolute dichloromethane (200 ml), triethylamine (84 ml) was dropwise added. After complete addition and stirring for further 6 h at room temperature, the reaction mixture was poured into water (150 ml), the organic layer was separated and the aqueous phase was further extracted with dichloromethane (2×200 ml). The combined organic extracts were washed with HCl 1N (2×200 ml), with saturated NaCl solution (2×200 ml), dried over magnesium sulphate and evaporated under reduced pressure. The obtained slightly yellow oil was chromatographed on silica (diethylether/petroleumether: 1/3) to give (s)-2-methyl-butyl p-toluenesulphonate as a colourless oil (Yield: 10.0 g, 89%).

Tris-1,2,3-[(S)-2-Methyl-butoxy]-benzene

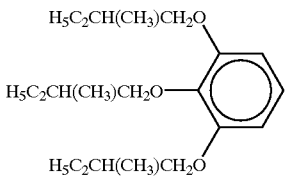

Under nitrogen atmosphere, a mixture of pyrogallol (1.26 g, 10 mmol), (S)-2-methylbutyl p-toluenesulphonate (8 g, 33 mmol) and potassium carbonate (5.53 g, 40 mmol) in dry DMF (20 ml) was stirred at 100° C. for 24 h. The cooled reaction mixture was gently poured into HCl 3N (60 ml) and extracted with diethylether (3×100 ml). The combined organic extracts were washed with 150 ml of saturated NaCl solution, dried over magnesium sulphate and evaporated under reduced pressure. The obtained oily residue was chromatographed on silica (dichloromethane/petroleumether: 1/1) to give tris-1,2,3-[(S)-2-methyl-butoxy]-benzene as a transparent oil (Yield: 2.4 g, 71%).

Tris-2,3,4-[(S)-2-Methyl-butoxy]-benzaldehyde

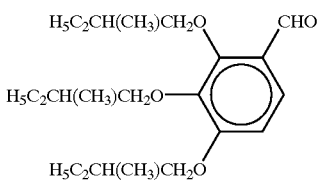

To a cooled (ice-water +10° C.) mixture of tris-1,2,3-[(S)-2-methyl-butoxy]-benzene (2 g, 6 mmol) and N-methylformanilide (1.62 g, 12 mmol), phosphorus oxychloride (11 g, 7.2 mmol) was added dropwise. After complete addition (10 min), the reaction mixture was stirred at room temperature for 2 h and at 60° C. for 1 h. To the cooled reaction mixture, 50 g of ice were added followed by slow addition of 5N NaOH solution until a pH of 6 was reached. This mixture was extracted twice with 150 ml of diethylether and the combined organic extracts were washed with 100 ml of HCl 3N and with 150 ml of saturated NaCl solution. The organic phase was dried over magnesium sulphate and evaporated under reduced pressure to afford a oily residue which was chromatographed on silica (diethylether/petroleumether: 1/3) to give tris-1,2,3-[(S)-2-methyl-butoxy]-benzaldehyde as a slightly yellow oil (Yield: 1.7 g, 78%).

2-Hydroxy-3,4-bis-[(S)-2-methyl-butoxy]-benzaldehyde

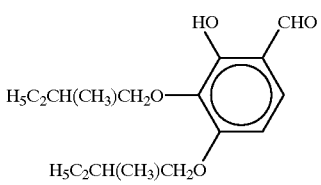

Tris-2,3,4-[(S)-2-methyl-butoxy]benzaldehyde (1.2 g, 3.3 mmol) is dissolved in CH$_2$Cl$_2$ (30 ml) and the obtained solution was cooled at −76° C. (acetone-dry ice bath) and maintained under nitrogen atmosphere. A solution of boron tribromide (0.32 ml, 3.3 mmol) in CH$_2$Cl$_2$ (10 ml) was added dropwise to the stirred solution. When the addition was complete (1 h), the reaction mixture was stirred for 4 h at −76° C. The reaction mixture was then hydrolyzed by careful shaking with 30 g of ice-water with continuous stirring for 30 min. The obtained brownish mixture was extracted with 3×50 ml of diethylether and the combined organic extracts were washed with saturated NaCl solution (2×50 ml), dried over magnesium sulphate and evaporated to dryness. The obtained brown residue was chromatographed on silica (diethylether/petroleumether: 1/3) to give 2-hydroxy-3,4-bis-[(S)-2-methyl-butoxy]-benzaldehyde as a slightly red oil (Yield: 0.76 g, 78%).

3,4-Bis-[(S)-2-Methyl-butoxy]-2-(pent-4-enyloxy)-benzaldehyde

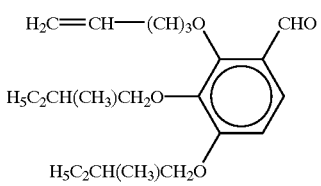

Under nitrogen atmosphere, a mixture of 2-hydroxy-3,4-bis-[(S)-2-methyl-butoxy]-benzaldehyde (0.74 9, 2.51 mmol), 5-bromo-1-pentene (0.45 g, 3.02 mmol) and potassium carbonate (0.41 g, 3 mmol) in dry DMF (5 ml) was stirred at 80° C. for 3 h. The cooled reaction mixture was gently poured into HCl 3N (15 ml) and extracted with diethylether (3×20 ml). The combined organic extracts are washed with 30 ml of saturated NaCl solution, dried over magnesium sulphate and evaporated under reduced pressure. The obtained oily residue was chromatographed on silica (diethylether/petroleumether: 1/3) to give 3,4-bis-[(S)-2-methyl-butoxy]-2-(pent-4-enyloxy)-benzaldehyde as a slightly yellow oil (Yield: 0.82 g, 90%).

(3,4-Dihydroxy-phenyl)-acetonitrile

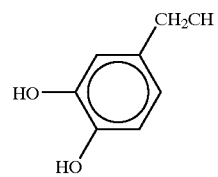

3,4-Dimethoxy-phenyl)-acetonitrile (8.86 g, 50 mmol) was dissolved in CH$_2$Cl$_2$ (200 ml) and the obtained solution was cooled at −76° C. (acetone-dry ice bath) and maintained under nitrogen atmosphere. A solution of boron tribromide (11.56 ml, 120 mmol) in CH$_2$Cl$_2$ (120 ml) was added dropwise to the stirred solution. As the solution of boron tribromide was added, a white precipitate was formed. When the addition was complete (30 min), the reaction mixture was allowed to attain room temperature overnight with stirring. The reaction mixture was then hydrolyzed by careful shaking with 200 g of ice-water, thus precipitating a white solid which was dissolved by the addition of 800 ml of diethylether. The organic layer was separated and the aqueous layer was saturated with NaCl and further extracted with 3×200 ml of diethylether. The combined organic extracts were washed with saturated NaCl solution (2×300 ml), dried over magnesium sulphate and evaporated to dryness to afford (3,4-dihydroxy-phenyl)-acetonitrile as white solid with a pinkish tint (Yield: 6.9 g, 92%).

(3,4-bis-Heptyloxy-phenyl)-acetonitrile

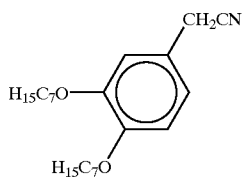

Under nitrogen atmosphere, a mixture of (3,4-Dihydroxy-phenyl)-acetonitrile (1.49 g, 10 mmol) 1-iodo-heptane (4.97 g, 22 mmol) and potassium carbonate (2.76 g, 20 mmol) in dry DMF (20 ml) was stirred at 70° C. for 6 h. The cooled reaction mixture was gently poured in HCl 3N (80 ml) and extracted with diethylether (3×150 ml). The combined organic extracts were washed with 150 ml of saturated NaCl solution, dried over magnesium sulphate and evaporated under reduced pressure. The obtained yellow oily residue was chromatographed on silica (diethylether/petroleumether: 1/2) to afford (3,4-bis-heptyloxy-phenyl)-acetonitrile as slightly yellow oil which solidified upon standing (Yield: 2.6 g, 75%).

2(3,4-bis-Heptyloxy-phenyl)-3-[3,4-bis-((S)-2-methyl-butoxy)-2-(pent-4enyloxy))-phenyl]-acrylonitrile

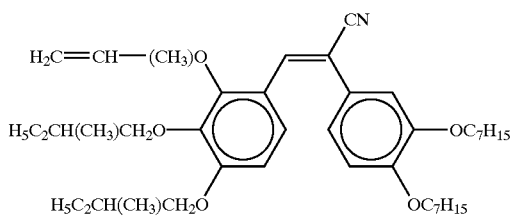

To a stirred solution of 3,4-Bis-[(S)-2-methyl-butoxyl]-2-(pent-4-enyloxy)-benzaldehyde (0.725 g, 2 mmol) and (3,4-Bis-heptyloxy-phenyl)-acetonitrile (0.691 g, 2 mmol) in 10 ml of absolute ethanol, cooled at 0° C. and maintained under nitrogen atmosphere, sodium ethylate (0.408 g, 6 mmol) was portionwise added (10 portions, 1 portion/2 min). After complete addition and stirring for further 12 h at room temperature the reaction mixture was poured into 30 ml of water and extracted with diethylether (3×50 ml). The combined organic extracts were washed with 60 ml of saturated NaCl solution, dried over magnesium sulphate and evaporated under reduced pressure. The obtained yellow oily residue was chromatographed on silica (diethylether/petroleumether: 1/3) to afford (3,4-bis-heptyloxy-phenyl)-acetonitrile as a slightly yellow oil which solidified upon standing (Yield: 1.2 g, 88%).

6,7-bis-Heptyloxy3,4-bis-[(S)-2-methyl-butoxy]-2-(pent-4-enyloxy)-phenanthrene-9-carbonitrile

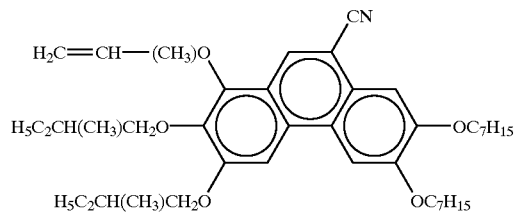

2-(3,4-Bis-heptyloxy-phenyl)-3-[3,4-bis((S)-2-methyl-butoxy)-2-(pent-4-enyloxy))-phenyl]-acrylonitrile (1.03 g, 1.51 mmol) was dissolved in absolute dichloromethane (20 ml) and the obtained solution was cooled to 0° C. and maintained under nitrogen atmosphere. A solution of boron trifluoride etherate (0.47 g, 3.32 mmol) in dichloromethane (3 ml) was dropwise added (within 15 min) to the reaction mixture which was stirred for further 15 min at 0° C. At this temperature, pyridiniumchlorochromate (PCC) (0.65 g, 3.02 mmol) was portionwise added (10 portions, 1 portion/min) to the reaction mixture which turned dark-green. After complete addition of PCC, the reaction mixture was stirred for further 10 min at room temperature, poured into water (20 ml), and extracted with dichloromethane (2×20 ml). The combined organic extracts were dried over magnesium sulphate and evaporated under reduced pressure. The obtained brown residue was chromatographed on silica (diethylether/petroleumether: 1/3) to afford the titled phenanthrene as orange-yellow pasty residue. In order to remove this coloration the above residue was filtered through a short column of neutral alumina (diethylether/petroleumether: 1/6). This gave the desired phenanthrene as white liquid-crystalline material (Yield: 0.91 g, 88%)

Compound (2) exhibits a monotropic columnar discotic phase and shows the phase behaviour K 66.5 (D 62.6) I.

The following compounds comprising a polymerizable reactive group have been prepared analoguously

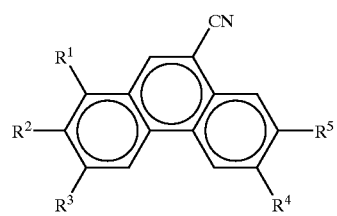

(2a–f)

| No. | $R^1$ | $R^2$ | $R^3$ | $R^4$ | $R^5$ | Phase Behaviour |
|---|---|---|---|---|---|---|
| 2a | 11-en | $OC_5H_{11}$ | $OC_5H_{11}$ | $OC_7H_{15}$ | $OC_7H_{15}$ | D 33.3 I |
| 2b | 11-en | $OC_6H_{13}$ | $OC_6H_{13}$ | $OC_6H_{13}$ | $OC_6H_{13}$ | K 30.8 (D 28) I |
| 2c | 5-en | $OC_6H_{13}$ | $OC_6H_{13}$ | $OC_6H_{13}$ | $OC_6H_{13}$ | K 52.3 (−13.4) D 67 I |
| 2d | 6-en | $OC_6H_{13}$ | $OC_6H_{13}$ | $OC_6H_{13}$ | $OC_6H_{13}$ | K 51.4 (−16.7) D 67.5 I |
| 2e | 11-en | $OC_7H_{15}$ | $OC_7H_{15}$ | 11-en | 11-en | K 11.9 (−25.4) D 31.3 I |
| 2f | 11-en | $OC_6H_{13}$ | $OC_6H_{13}$ | 11-en | 11-en | K 24 I |

11-en = undec-10-enoxy, 6-en = hex-5-enoxy, 5-en = pent-4-enoxy

EXAMPLE 2b

The electrooptic behaviour of compound (2c) was investigated. A sample of compound (2c) was put into a cell consisting of two glass plates separated by glass spacers at a distance of 10 μm and partially coated by a conductive layer of indium tin oxide (ITO). The sample spontaneously aligned homeotropically. Then a low frequency AC electric field (1 Hz) was applied to the cell.

Figure 2A:
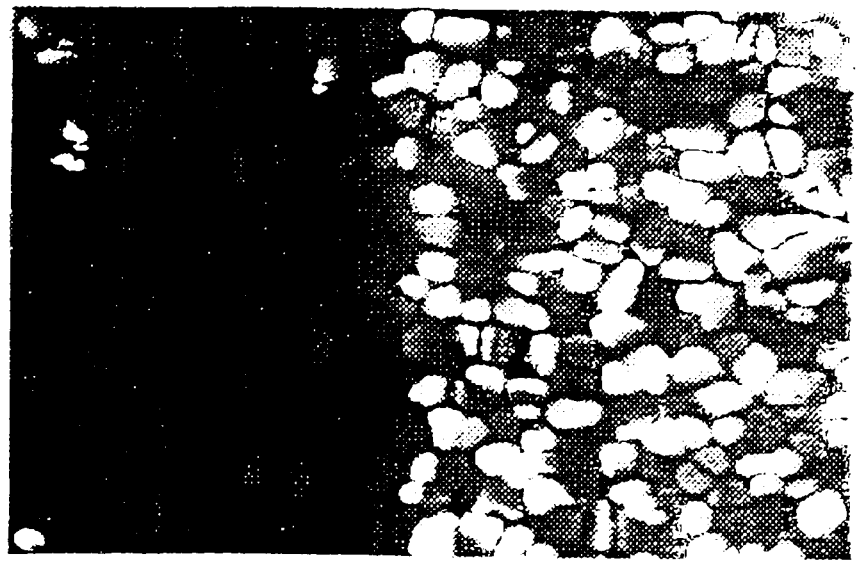
FIGS. 2A and 2B show an inventive discotic liquid crystalline compound according to example 2 between crossed nicol polarizers upon application of an electric field.
Figure 2B:

FIGS. 2A and 2B depict the sample between crossed nicol polarizers upon application an electric field of 4 V/$\mu$m (FIG. 2A) and 10 V/$\mu$m (FIG. 2B) respectively. The right sides of FIGS. 2A and 2B show the sample between the ITO-coated, conductive parts of the glass plates, the left sides show the sample between the non-conductive parts of the glass plates.

Upon application of an electric field of 4 V/$\mu$m, the sample switched between the initial homeotropic orientation and a highly bright state (FIG. 2A). When the electric field was increased to 10 V/$\mu$m, the birefringence of the sample increased to yield a pseudo focal-conic texture (FIG. 2B), which is characteristic for columnar mesophases.

At the higher field of 10 V/$\mu$m, the switching of the sample in the slow AC field ceased visually and the initial homeotropic could only be recovered by heating the sample to the isotropic phase, followed by recooling to the discotic phase.

EXAMPLE 3a

The elastomers (3a) to (3h) have been prepared from the monomers (2b) to (2d) and the crosslinkers (2e), (2f) and (v) shown in table 2 by the following methods which is described in detail for elastomer (3c):

60.12 mg (1 mmol of SiH groups) of poly[oxo (methylsilylene)], 584.8 mg (0.85 mmol) of mesogen (2c(, 49.82 mg (0.05 mmol) of cross-linker (2e) and 5 $\mu$l of platinum catalyst SLM 85006 (Wacker Chemie Burghausen) were dissolved in 1 ml of absolute toluene and the obtained solution was filtered using a 0.5 mm Millipore filter and filled into a centrifuge cell with a diameter of 5 cm and a height of 1 cm, excluding dust particles. To avoid tack, the inner wall of the cell is covered with a teflon film. The reaction was carried out under centrifugation (4000 rpm) at 60° C. for 2 h. Thereafter the whole cell is cooled to room temperature and the swollen elastomer is carefully removed from the cell. The swollen elastomer is fixed at one end with an clamp and uniaxially strained by a stress applied from the other end of the film. It was then annealed for 24 h at room temperature, to complete the cross-linking reaction. This leads to a transparent liquid-crystalline sample.

The polydomain sample is prepared under similar conditions, however, without load during the deswelling process.

Elastomers (3a,b) and (3d–h) have been prepared analoguously.

TABLE 2

| Structure | n | m | No. |
|---|---|---|---|
| CH$_2$=CH—(CH$_2$)$_n$—O— [triphenylene with CN, H$_{13}$C$_6$O, H$_{13}$C$_6$O, OC$_6$H$_{13}$, OC$_6$H$_{13}$] | 9 | — | 2b |
|  | 3 | — | 2c |
|  | 4 | — | 2d |
| CH$_2$=CH—(CH$_2$)$_9$—O— [triphenylene with CN, H$_{2m+1}$C$_m$O, H$_{2m+1}$C$_m$O, O(CH$_2$)$_9$—CH=CH$_2$, O(CH$_2$)$_9$—CH=CH$_2$] | — | 7 | 2e |
|  | — | 6 | 2f |
| CH$_2$=CH—(CH$_2$)$_9$—O—[phenyl]—O(CH$_2$)$_9$—CH=CH$_2$ | — | — | v |

The elastomers exhibit the following phase behaviour

| No. | Monomer | Crosslinker | Reaction Time (h) | Phase Behaviour | $\Delta$H (kJ/mol) |
|---|---|---|---|---|---|
| 3a | 2b | v | 1.5 | G-23 I | — |
| 3b | 2b | 2e | 1.5 | G-17 I | — |
| 3c | 2c | 2e | 24 | G-19 D 50 I | 1.2 |
| 3d | 2c | 2e | 72 | G-24 D 48 I | 2.2 |
| 3e | 2c | v | 72 | G-31 D 52 I | 1.1 |
| 3f | 2d | v | 1 | G-14 I | — |
| 3g | 2d | v | 48 | G-18 I | — |
| 3h | 2d | 2f | 1 | G-8 I | — |

The elastomers (3c) to (3e) prepared from monomer (2c) with a pentyl spacer exhibit a broad columnar discotic phase independently from the type of crosslinker used, whereas in the elastomers prepared from monomer (2b) and (2d) with a hexyl and undecenyl spacer the mesophase is suppressed below the glass transition.

This is in accordance with the phase behaviour of the corresponding monomers of example 2, wherein compound (2c) with a short spacer has a broader discotic phase and a higher clearing point than compound (2b) with a long spacer.

Furthermore, in the case of monomer (2c) a longer hydrosilylation reaction time was required to form the networks (3c) to (3e). In contrast to that, in the case of monomer (2d) the network was obtained within 1 h only and a prolonged reaction time had no further effect, as can be taken from the comparison of (3f) and (3g).

Thus, an increase of the spacer length of only one $CH_2$ group has a considerable effect on the stability of the columnar mesophase of the elastomer and also on the efficiency of the polymerization reaction.

EXAMPLE 3b

The anisotropy of the networks of example 3a was investigated by swelling experiments. Isotropic networks swell identically in the three dimensions, whereas anisotropic networks obtained by uniaxial stress swell less in the direction of the stress axis than in the direction perpendicular to the stress axis.

The results of the swelling experiments of poly- and monodomain elastomers (3c) and (3e) in toluene are outlined in table 3. The samples (I) and (II) are unstrained polydomain networks, whereas (III) and (IV) have been strained during their synthesis as described above. Sample (V) has been strained in the isotropic state and recooled to the discotic liquid crystalline state.

In table 3, $\alpha_\parallel$ and $\alpha_\perp$ denote the swelling coefficients respectively parallel and perpendicular to the stress axis and are defined as the ratio of the respective network dimension in the swollen and the unswollen state. The anisotropy of the network is given by the ratio $\alpha_\perp/\alpha_\parallel$. The degree of swelling $q=\alpha_\perp\alpha_\parallel^2$ is related to the average molar mass of the strands of the network, and is thus a function of the cross-linking density.

TABLE 3

| Sample | Elastomer | Stress (N · mm$^{-2}$) | $\alpha_\parallel$ | $\alpha_\perp$ | $\alpha_\perp/\alpha_\parallel$ | q |
|---|---|---|---|---|---|---|
| I | 3c | 0 | 1.6 | 1.7 | 1.1 | 4.6 |
| II | 3e | 0 | 1.6 | 1.6 | 1.0 | 4.1 |
| III | 3c | 0.009 (during synthesis) | 1.2 | 2.0 | 1.7 | 4.8 |
| IV | 3e | 0.012 (during synthesis) | 1.1 | 1.9 | 1.7 | 4.0 |
| V | 3e | 0.011 (at isotropic state) | 1.1 | 2.0 | 1.8 | 4.4 |

The data in table 3 show that the unstrained polydomain networks (I) and (II) swell isotropically, whereas the networks prepared with uniaxial stress during their synthesis (III, IV) or being strained in the isotropic state (V) swell anisotropically, as indicated by their higher swelling coefficients in the direction perpendicular to the stress axis.

EXAMPLE 3c

The columnar discotic phases of elastomers (3c) and (3e) have been further investigated by X-ray experiments. The results are depicted in FIGS. 3A to 3E and FIGS. 4A to 4D.

Figure 3A:
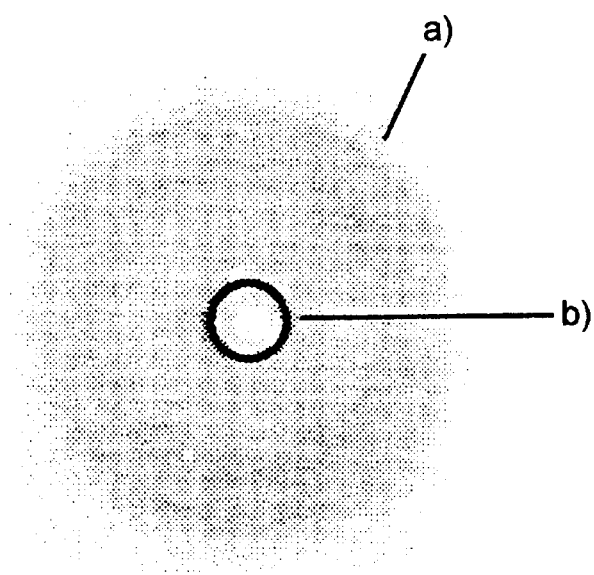
FIGS. 3A to 3D show the X-ray diffraction pattern of samples of an inventive discotic liquid crystalline elastomer according to example 3.
Figure 3B:
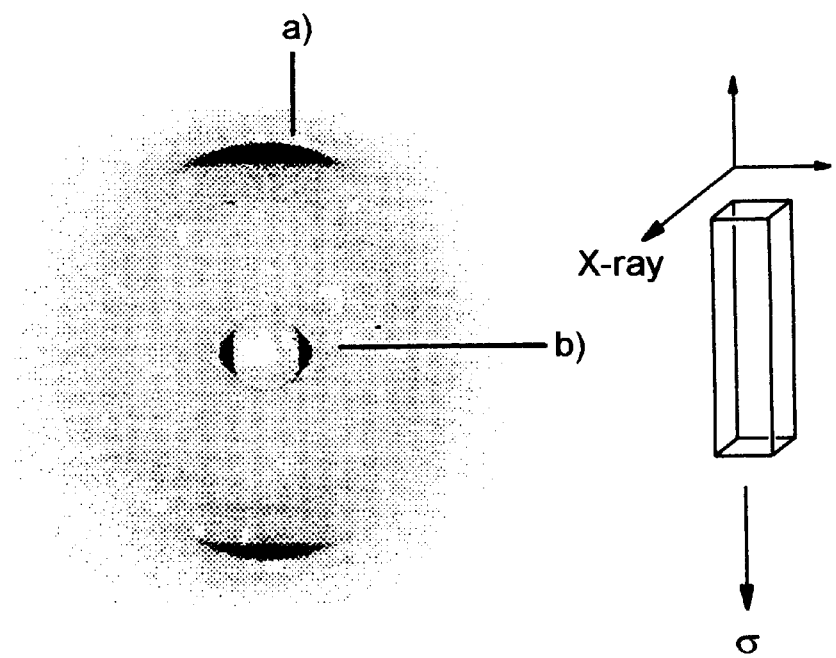
Figure 3C:
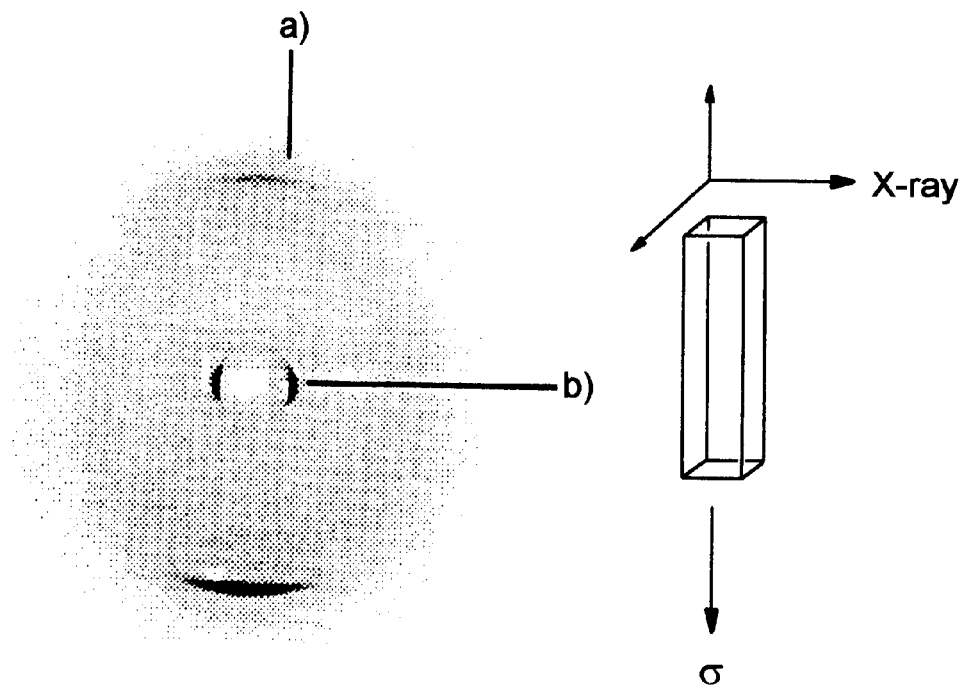
Figure 3D:
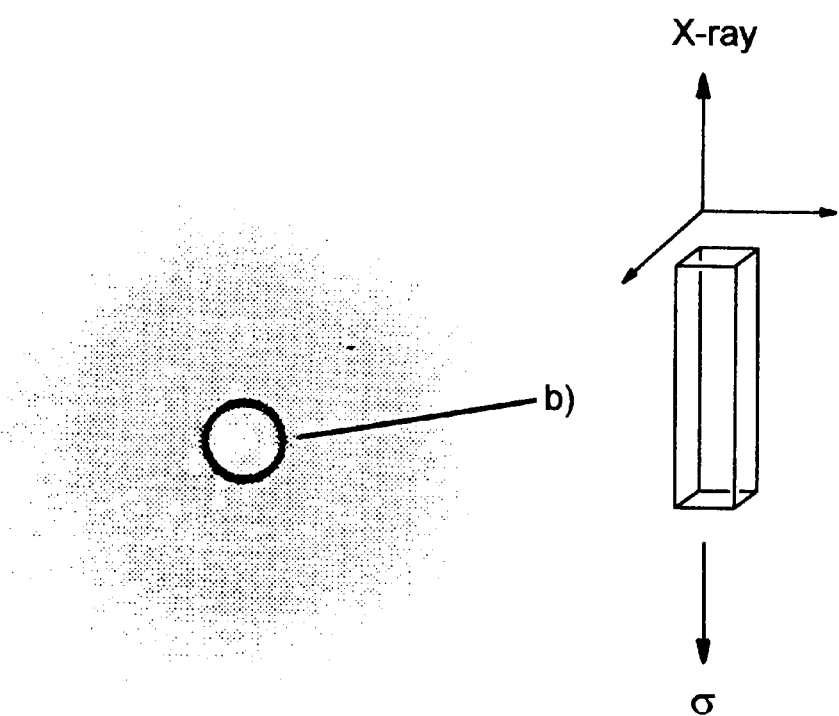

FIGS. 3A to 3D show the X-ray diffraction pattern of two samples of elastomer (3c) in its columnar discotic phase at room temperature, with FIG. 3A refering to a polydomain sample, and FIGS. 3B to 3D refering to a monodomain sample.

In FIGS. 3B and 3C, the incident X-ray beam is perpendicular to the surface of the detector and to the stress direction, whereas in FIG. 3D the incident beam is parallel to the stress direction. The spatial relationship between the network sample, the axis of stress a and the direction of incidence of the X-ray beam is depicted in the FIGS. 3B to 3D.

Two reflections are shown: The wide angle reflection (a) is attributed to the intracolumnar disk spacing while the small angle reflection (b) is due to the intermolecular disk spacing.

For the polydomain sample (FIG. 3A), the distribution of the liquid crystalline director is isotropic, corresponding to a homogeneous azimuthal distribution of the X-ray intensities.

For the monodomain samples, when being viewed at perpendicular to the stress direction, the distribution of the director is anisotropic, corresponding to sharp maxima in the azimuthal distribution of the intensities (FIGS. 3B and 3C). Of these, the wide angle reflection maxima (a) are parallel to the stress axis and the small angle maxima (b) are perpendicular to the stress axis. This demonstrates clearly that the columns are macroscopically oriented parallel to the stress axis, which is in agreement with the results of the swelling experiments.

In accordance with that, in case of the incident X-ray beam being parallel to the stress axis (FIG. 3D), although the sample is a monodomain, only the small angle reflection (b) corresponding to the intercolumnar disk spacing is observed, and the reflection pattern is isotropic, since the liquid crystal director and thus the anisotropy of the columnar phase are not detectable when viewing in the direction parallel to the columns.

Figure 3E:
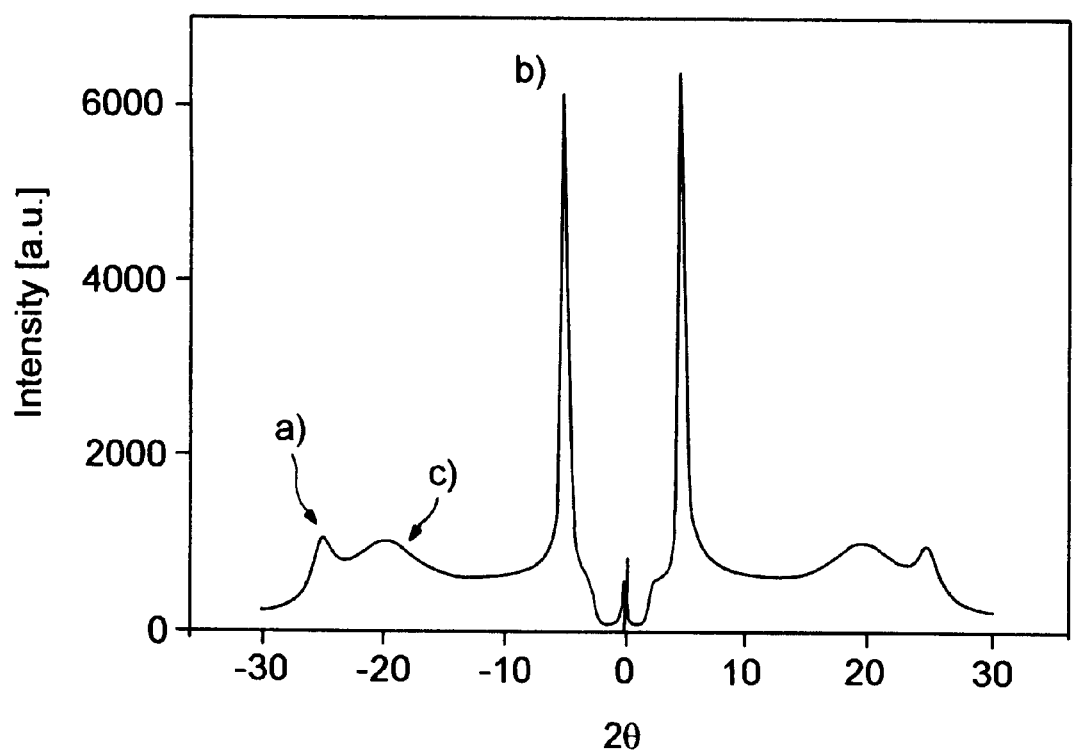
FIG. 3E shows the azimuthal intensity distribution of the diffraction pattern of FIG. 3A.

The azimuthal intensity distribution of the diffraction pattern of the polydomain sample (i.e. a scan across FIG. 3A in any direction) is depicted in FIG. 3E and shows a maximum a) at an angle 2θ of 24.7°, corresponding to a molecular distance d of 3.6 Å (intracolumnar correlation, 11 molecules), a maximum b) at an angle of 4.7°, corresponding to a molecular distance of 17.9 Å (intercolumnar correlation, 9 columns), and a maximum c) at an angle of 19.7°, corresponding to a molecular distance of 10.3 Å.

Figure 4A:
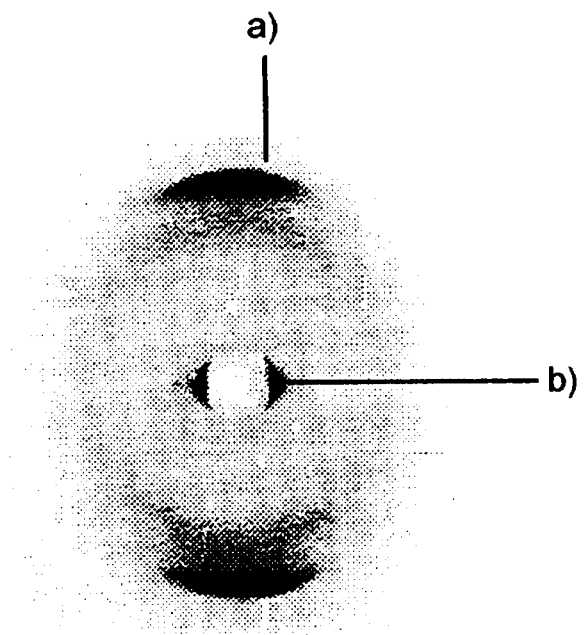
FIGS. 4A and 4B show the X-ray diffraction pattern of samples of an inventive discotic liquid crystalline elastomer according to example 3.
Figure 4B:
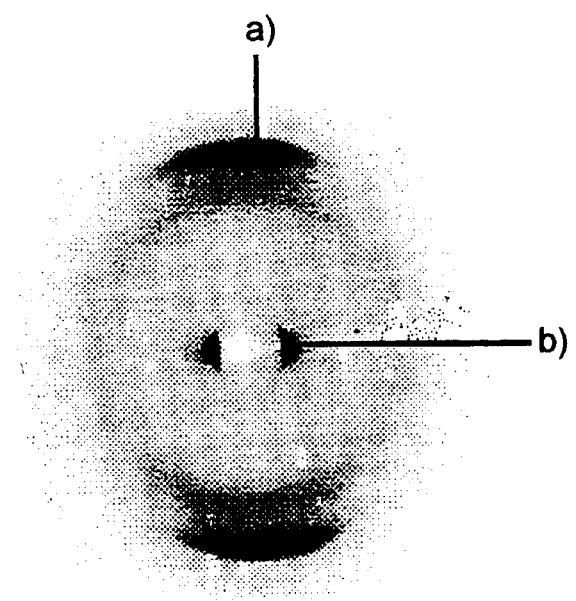

FIGS. 4A and 4B show the X-ray diffraction pattern at room temperature of two polydomain samples of elastomer (3e) that have been oriented by mechanical stress. The incident X-ray beam is perpendicular to the surface of the detector and to the stress direction. FIG. 4A refers to a sample that is strained in the discotic liquid crystalline phase. FIG. 4B refers to a sample that has been strained in the isotropic state and recooled to the discotic phase.

In both states, the director is anisotropic, corresponding to sharp maxima in the azimuthal intensity distribution of the wide angle reflection (a) parallel and the small angle reflection (b) perpendicular to the stress axis.

Figure 4C:
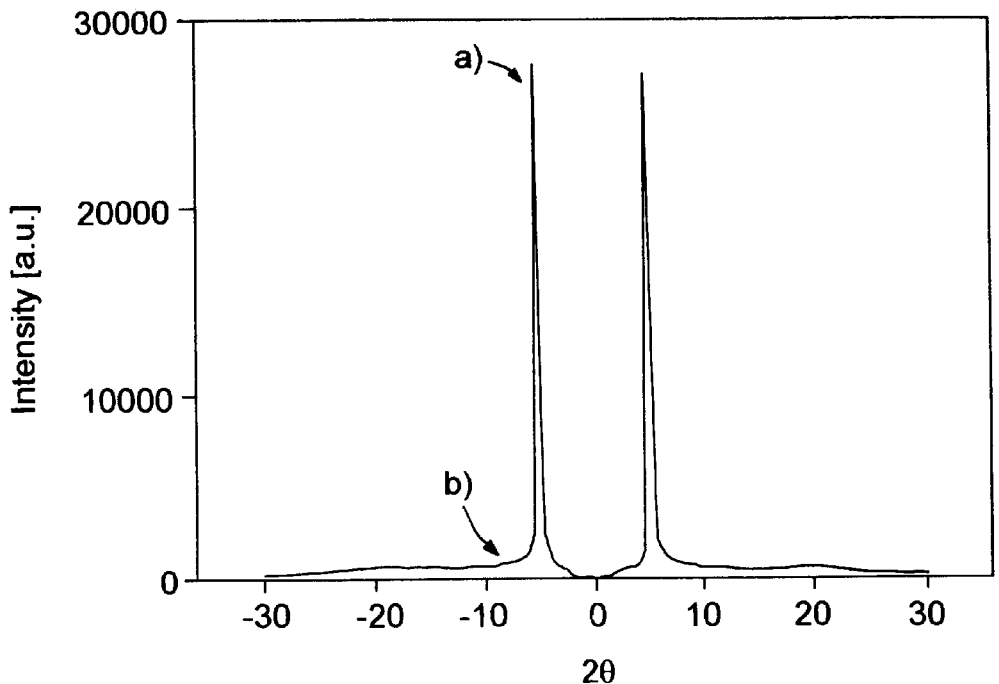
FIGS. 4C and 4D show the azimuthal intensity distribution of the diffraction pattern of FIG. 4A in horizontal and vertical directions respectively.
Figure 4D:
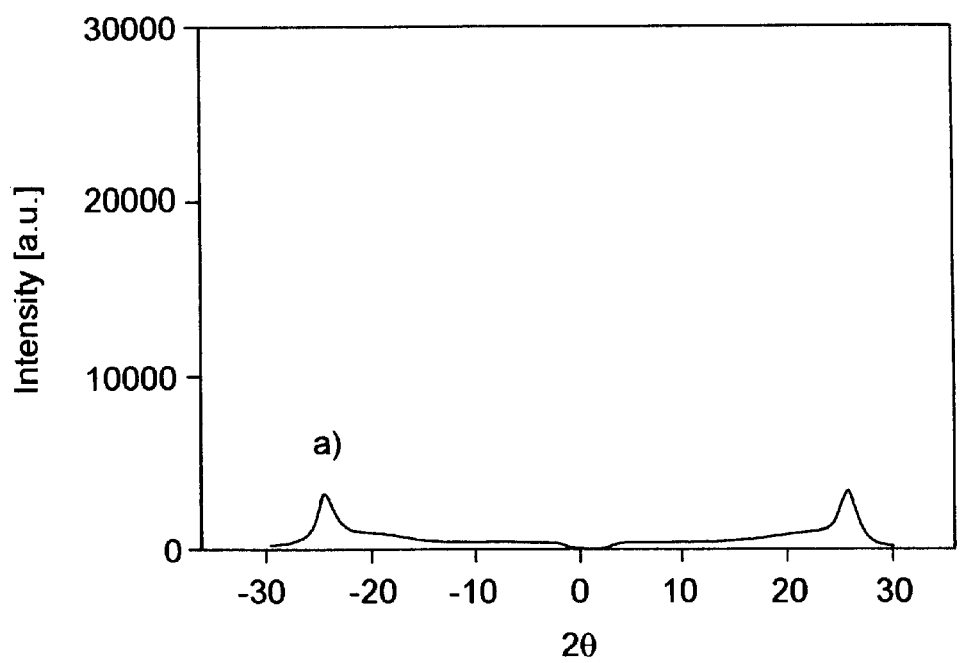

The azimuthal intensity distribution of the diffraction pattern of FIG. 4A is shown in FIGS. 4C and 4D, with FIG. 4C depicting the small angle reflection (i.e. a scan across FIG. 4A in horizontal direction) and FIG. 4D the wide angle reflection (i.e. a scan across FIG. 4A in vertical direction). The reflection maximum a) in FIG. 4C at an angle 2θ of 5.07°, corresponding to a distance of 17.7 Å, is showing the intercolumnar correlation (14 columns). The reflection peak b) in FIG. 4C at an angle 2θ of 8.6°, corresponding to a distance of 10.3 Å is showing the hexagonal second order diffraction and indicates a hexagonal lattice of the columns. The reflection maximum a) in FIG. 4D at an angle 2θ of 25°, corresponding to a distance of 3.6 Å, is attributed to the intercolumnar correlation (11 molecules). It can be seen that the peaks a) in FIG. 4C and a) in FIG. 4D are perfectly separated.

These results show that the discotic columns are macroscopically oriented parallel to the stress axis, and are in good agreement with the results of the swelling experiments.

EXAMPLE 4

The following compounds have been prepared

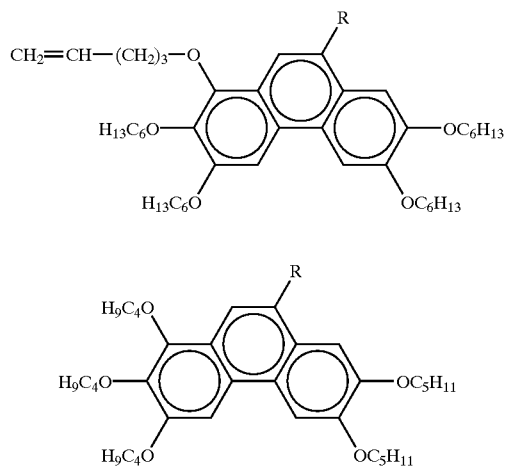

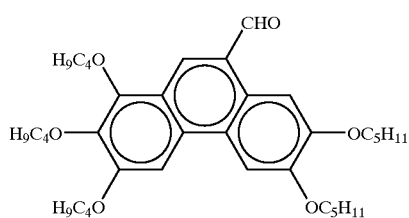

| Compound No. | 4a | 4b | 4c | 4d | 4e | 4f |
|---|---|---|---|---|---|---|
| Formula | A | A | B | B | B | B |
| R | CN | CHO | CN | CHO | 7-enOH | 7-enO |

7-enOH = —CH(OH)—$(CH_2)_4$—CH=$CH_2$, 7-enO = —CO—$(CH_2)_4$—CH=$CH_2$

Compounds (4a) and (4c) wherein R is CN have been prepared as described in examples 1 and 2a. The compounds (4d) to (4f) have been prepared from compound (4c) by transformation of the cyano group as described below. Compound (4b) was obtained in an analoguous manner from compound (4a).

1,2,3-Tributoxy-6,7-bis-pentyloxy-phenanthrene-9-carbaldehyde (4d)

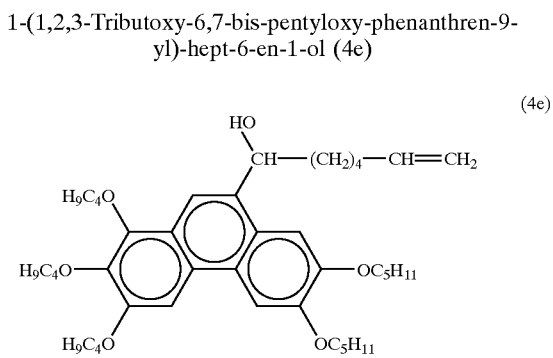

A solution of diisobuthylaluminohydride (1M in toluene, 10 ml, 10 mmol) was added dropwise, under a nitrogen atmosphere to a solution of 1,2,3-tributoxy-6,7-bis-pentyloxy-phenanthrene-9-carbonitrile (2.96 g, 5 mmol) in dry toluene (50 ml), cooled at −76° C.

After complete addition of the hydride (1 h), the obtained yellow solution was stirred at −76° C. for 2 h, then at room temperature for 3 h. The reaction mixture was then cooled at 0° C and 10 ml of methanol were added followed by dropwise addition of 150 ml of cold 5N sulfuric acid. After stirring for 5 h at room temperature, the yellow-orange reaction mixture was extracted with diethylether (4×200 ml) and the combined ether extracts were washed with saturated $NaHCO_3$ solution (300 ml), with saturated NaCl solution (2×200 ml), dried over magnesium sulphate and evaporated to dryness. The obtained yellow-orange oily residue was chromatographed on silica (dichloromethane/ petroleumether: 2/1) to afford 1,2,3-tributoxy-6,7-bis-pentyloxy-phenanthrene-9-carbaldehyde as yellow liquid-crystalline material which crystallised upon standing (Yield 2.43 g, 82%).

1-(1,2,3-Tributoxy-6,7-bis-pentyloxy-phenanthren-9-yl)-hept-6-en-1-ol (4e)

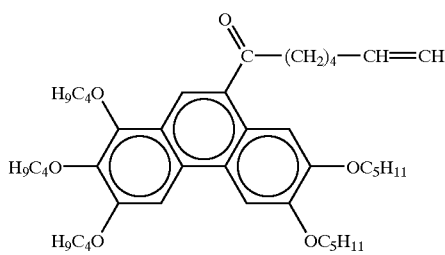

To a suspension of magnesium (98 mg, 4 mmol) in dry THF (8 ml), a solution of 6-bromo-1-hexene (0.65 9, 4 mmol) in dry THF (2 ml) was added under a nitrogen atmosphere and the obtained reaction mixture was stirred at room temperature until complete consummation of the metal. This mixture was then added dropwise under a nitrogen atmosphere to a solution of 1,2,3-tirbutoxy-6,7-bis-pentyloxy-phenanthrene-9-carbaldehyde (2 g, 3.36 mmol) in dry toluene (20 ml) cooled at 0° C. After complete addition of the grignard reagent (15 min) the reaction mixture was stirred for 1 h at 0° C. then quenched with 50 ml of HCl 1N. The obtained mixture was extracted with diethylether (3×80 ml) and the combined ether extracts were washed with saturated NaCl solution (2×80 ml), dried over magnesium sulphate and evaporated to dryness. The obtained oily residue was chromatographed on silica (dichloromethane) to afford 1-(1,2,3-tributoxy-6,7-bis-pentyloxy-phenanthren-9-yl)-hept-6-en-1-ol as colourless oil which crystallised upon standing (Yield 1.9 g, 83%).

1-(1,2,3-Tributoxy-6,7-bis-pentyloxy-phenanthren-9-yl)-hept-6-en-1-one (4f)

To a suspension of 1.4 mmol/g of pyridinium chlorochromate on basic alumina (3.2 g, 4.5 mmol of PCC) in hexane (20 ml) a solution of 1-(1,2,3-tributoxy-6,7-bis-pentyloxy-phenanthren-9-yl)-hept-6-en-1-ol (1.02 g, 1.5 mmol) in hexane (30 ml) was added under a nitrogen atmosphere and the obtained mixture was stirred at room temperature for 5 h (the original orange coloration of the suspension turned brown). The reaction mixture was then filtered and the black alumina residue was further washed with 100 ml of hexane. After evaporation of hexane the obtained slightly orange residue was filtered over short silica-gel column (diethylether (hexane: 1/1) to afford 1-(1,2,3-tributoxy-,6,7-bis-pentyloxy-phenanthren-9-yl)-hept-6-en-1-one as yellow liquid-crystalline material (Yield 0.92 g, 91%).

The compounds show the following phase behaviour

| No. | Formula | R | Phase Behaviour | ΔH (kJ/mol) |
|---|---|---|---|---|
| 4a | A | CN | K 52.3 (−13.4) D 67 I | 2.2 |
| 4b | A | CHO | K 38 D 44.5 I | 3.1 |
| 4c | B | CN | K (30 D 77) 81 I | — |
| 4d | B | CHO | K 49.5 (−25.3) D 63.5 I | 3.86 |
| 4e | B | 7-enOH | K 50.7 I | — |
| 4f | B | 7-enO | K 21.5 (20.6) D 66.2 I | 7.1 |

7-enOH = —CH(OH)—(CH$_2$)$_4$—CH=CH$_2$, 7-enO = —CO—(CH$_2$)$_4$—CH=CH$_2$

In case of compounds of formula A, the cyano-substituted compound (4a) exhibits a higher stability of the discotic phase, with a higher clearing point than the corresponding aldehyde (4b).

In case of compounds of formula B with shorter alkoxy substituents, the aldehyde compound (4d) has a higher stability of the discotic phase, whereas the cyano compound (4c) shows even only a monotropic phase. The homologue (4e) with a hydroxy-substituted alkenyl group shows no mesophase at all, while the corresponding ketone (4f) exhibits a discotic phase with the highest stability of all compounds of example 4.

This indicates that discotic phenanthrenes of formula II wherein W is an electron withdrawing group show good discotic phase behaviour.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various conditions and usages.

What is claimed is:

1. A process of preparing a discotic liquid crystalline compound by intramolecular oxidative cyclisation of a diaryl compound in an organic solvent in the presence of a strong acid, wherein an oxidative agent comprising a chrom(VI)oxide derivative is used.

2. A process according to claim 1 of preparing a discotic liquid crystalline compound of formula I

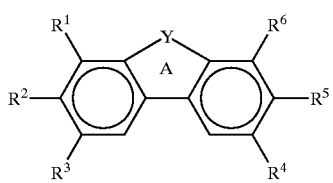

by intramolecular oxidative cyclisation of a diaryl compound of formula Ia

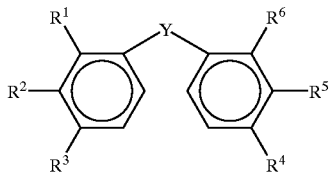

wherein

A is an aliphatic or aromatic five- or six-membered ring,

Y is —CH$_2$—, —NH—, —CH=CW—, —CO—, —COO—, or a radical >CH—CH< or >C=C< that is part of a mono- or bicyclic group comprising one or two condensated five- or six-membered aromatic or aliphatic rings, each of which may comprise one or more hetero atoms and may be unsubstituted, mono- or polysubstituted by R$^1$, W is halogen, a dipolar group selected from CN, NO$_2$, SO$_2$CH$_3$, SOCH$_3$, SOCF$_3$, SOOCH$_3$, SOOCF$_3$ or COR$^1$, or has one of the meanings of R$^1$, R$^1$ to R$^6$ are in each case independently H, straight-chain or branched alkyl with 1 to 15 C atoms which may be unsubstituted, mono- or polysubstituted by halogen or CN, it being also possible for one or more non-adjacent CH$_2$ groups to be replaced, in each case independently from one another, by —O—, —S—, —NH—, —N(CH$_3$)—, —CH(OH)—, —CO—, —COO—, —OCO—, —OCO—O—, —S—CO—, —CO—S—, —CH=CH— or —C≡C— in such a manner that oxygen atoms are not linked directly to one another, or alternatively one or more of R$^1$ to R$^6$ are denoting P—(Sp—X)$_n$—, P is a polymerizable group, Sp is a spacer group having 1 to 15 C atoms, X is group selected from —O—, —S—, —CO—, —COO—, —OCO—, —OCO—O—, —S—CO—, —CO—S— or a single bond, and n is 0 or 1.

3. A process according to claim 1, wherein the oxidative agent is a pyridinium complex or pyridinium complex salt of a chrom(VI) oxide derivative.

4. A process according to claim 1, wherein boron trifluoride etherate or trifluoroacetic acid is used as strong acid in the intramolecular cyclisation reaction.

5. A process according to claim 1 of preparing a discotic liquid crystalline phenanthrene derivative of formula II

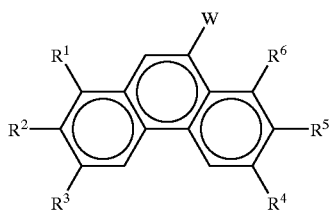

by intramolecular oxidative cyclisation of a stilbene derivative of formula IIa

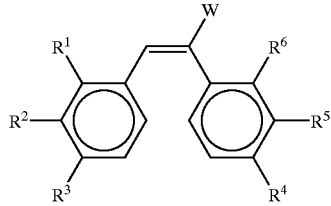

W is halogen, a dipolar group selected from CN, NO$_2$, SO$_2$CH$_3$, SOCH$_3$, SO$_2$CF$_3$, SOOCH$_3$, SOOCF$_3$ or COR$^1$, or has one of the meanings of R$^1$, R$^1$ to R$^6$ are in each case independently H, straight-chain or branched alkyl with 1 to 15 C atoms which may be unsubstituted, mono- or polysubstituted by halogen or CN, it being also possible for one or more non-adjacent CH$_2$ groups to be replaced, in each case independently from one another, by —O—, —S—, —NH—, —N(CH$_3$)—, —CH(OH)—, —CO—, —COO—, —OCO—, —OCO—O—, —S—CO—, —CO—S—, —CH=CH— or —C≡C— in such a manner that oxygen atoms are not linked directly to one another, or alternatively one or more of R$^1$ to R$^6$ are denoting P—(Sp—X)$_n$—, P is a polymerizable group, Sp is a spacer group having 1 to 15 C atoms, X is group selected from —O—, —S—, —CO—, —COO—, —OCO—, —OCO—O—, —S—CO—, —CO—S— or a single bond, and n is 0 or 1.

6. A process according to claim 5, wherein W is —CN, —CHO or P—(Sp—X)$_n$—.

7. A process according to claim 5, wherein at least two of R$^1$ to R$^6$ are each independently denoting straight-chain or branched alkoxy or alkenyloxy with 1 to 12 C atoms.

8. A process of according to claim 5, wherein at least one of R$^1$ to R$^6$ is denoting P—(Sp—X)$_n$.

9. A process according to claim 5, wherein P is a vinyl, vinyloxy, acrylate, methacrylate, chloroacrylate, epoxy or styrene group.

10. A process according to claim 5 of preparing a discotic liquid crystalline phenanthrene derivative of formula II by reacting the benzaldehyde IIb*

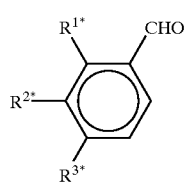

with the benzylcyanide IIc*

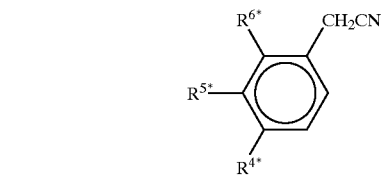

wherein R$^{1*}$ to R$^{6*}$ have one of the meanings of R$^1$, in the presence of a base to the cyanostilbene IIa*,

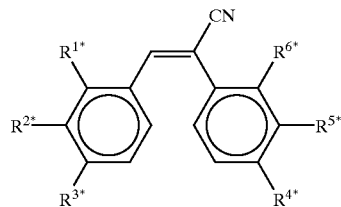

followed by intramolecular oxidative cyclisation of the cyanostilbene IIa* in an organic solvent in the presence of pyridinium chlorochromate (PCC) and a strong acid to give the phenanthrene II*,

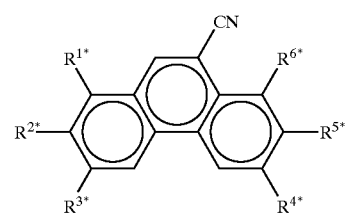

and optionally converting one or more of the groups R$^{1*}$ to R$^{6*}$ and/or the nitrile group of the phenanthrene II* by known methods into the desired substituents to give a phenanthrene derivative of formula II.

11. A process according to claim 10, wherein R$^{2*}$, R$^{3*}$, R$^{4*}$ and R$^{5*}$ are each independently denoting straight-chain or branched alkoxy or alkenyloxy with 1 to 12 C atoms.

12. A process of preparing compounds of formula I according to claim 2, wherein Y is —NH—, —CO—, —COO— or denotes

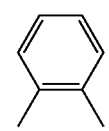

wherein the phenyl ring may be unsubstituted, mono- or polysubstituted by R$^1$ as defined in formula I.

13. A discotic liquid crystalline compound of formula I

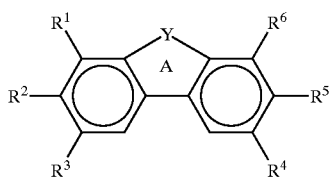

wherein

A is an aliphatic or aromatic five- or six-membered ring,

Y is —CH=CW—, —CO—, —COO—, or a radical >CH—CH< or >C=C< that is part of a mono- or bicyclic group comprising one or two condensed five- or six-membered aromatic or aliphatic rings, each of which may comprise one or more hetero atoms and may be unsubstituted, mono- or polysubstituted by $R^1$, W is halogen, a dipolar group or has one of the meanings of $R^1$, $R^1$ to $R^6$ are each independently H, straight-chain or branched alkyl with 1 to 15 C atoms which may be unsubstituted, mono- or polysubstituted by halogen or CN, one or more non-adjacent $CH_2$ groups optionally being replaced, in each case independently from one another, by —O—, —S—, —NH—, —N(CH$_3$)—, —CH(OH)—, —CO—, —COO—, —OCO—, —OCO—O—, —S—CO—, —CO—S—, —CH=CH— or —C≡C— in such a manner that oxygen atoms are not linked directly to one another, or one or more of $R^1$ to $R^6$ is P—(Sp—X)$_n$—, P is a polymerizable group, Sp is a spacer group having 1 to 15 C atoms, X is —O—, —S—, —CO—, —COO—, —OCO—, —OCO—O—, —S—CO—, —CO—S—, or a single bond, and n is 0 or 1, wherein at least one of $R^1$ to $R^6$ or W is P—(Sp—X)$_n$.

14. A liquid crystalline medium with a columnar phase comprising at least two components, at least one of which is a discotic liquid crystalline compound according to claim 13.

15. A linear or crosslinked liquid crystalline (co)polymer obtainable from discotic liquid crystalline compounds according to claim 13 by polymerization or polymeranaloguous reaction.

16. A discotic liquid crystalline compound according to claim 13, wherein Y is —CH=CW— and W is as defined in formula I.

17. A discotic liquid crystalline compound according to claim 13, wherein Y is >C=C< that is part of a phenylene ring which is unsubstituted, or mono- or polysubstituted by $R^1$ to $R^6$ as defined in formula I.

18. A discotic liquid crystalline compound of formula II

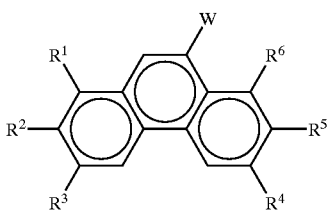

wherein

W is a halogen, a dipolar group or P—(Sp—X)$_n$—

$R^1$ to $R^6$ are each independently H, straight—chain or branched alkyl with 1 to 15 C atoms which may be unsubstituted, mono- or polysubstituted by halogen or CN, it being also possible for one or ore non-adjacent $CH_2$ groups to be replaced, in each case independently from one another, by —O—, —S—, —NH—, —N(CH$_3$)—, —CH(OH)—, —CO—, —COO—, —OCO—, —OCO—O—, —S—CO—, —CO—S—, —CH=CH— or —C≡C— in such a manner that oxygen atoms are not linked directly to one another, or one or more of $R^1$ to $R^6$ is P—(Sp—X)$_n$—, P is a polymerizable group, Sp is a spacer group having 1 to 15 C atoms, X is —O—, —S—, —CO—, —COO—, —OCO—, —OCO—O—, —S—CO—, —CO—S—, or a single bond, and n is 0 or 1.

19. A discotic liquid crystalline compound according to claim 16, wherein W is CN, F, Cl, CHO, COR$^1$ or P—(Sp—X)$_n$—.

20. A discotic liquid crystalline compound according to claim 13, wherein one, two or three of $R^1$ and $R^6$ are P—(Sp—X)$_n$—.

21. A discotic liquid crystalline compound according to claim 13, wherein P is a vinyl, vinyloxy, acrylate, methacrylate, chloroacrylate, epoxy or styrene group.

22. A discotic liquid crystalline compound according to claim 13, wherein W is CN, NO$_2$, SO$_2$CH$_3$, SOCH$_3$, SOCF$_3$, SOOCH$_3$, SOOCF$_3$ or COR$^1$.

23. A discotic liquid crystalline compound according to claim 18, wherein W is CN, NO$_2$, SO$_2$CH$_3$, SOCH$_3$, SOCF$_3$, SOOCH$_3$, SOOCF$_3$ or COR$^1$.

24. A discotic liquid crystalline compound according to claim 18, wherein W is CN, F, Cl, CHO, COR$^1$ or P—(Sp—X)$_n$—.

25. A discotic liquid crystalline compound according to claim 18, wherein one, two or three of $R^1$ and $R^6$ are P—(Sp—X)$_n$—.

26. A discotic liquid crystalline compound according to claim 18, wherein P is a vinyl, vinyloxy, acrylate, methacrylate, chloroacrylate, epoxy or styrene group.

27. A discotic liquid crystalline compound according to claim 13, obtainable by a process comprising intramolecular oxidative cyclisation of a diaryl compound in an organic solvent in the presence of a strong acid, wherein an oxidative agent comprising a chrom(VI)oxide derivative is used.

28. A discotic liquid crystalline compound according to claim 18, obtainable by a process comprising intramolecular oxidative cyclisation of a diaryl compound in an organic solvent in the presence of a strong acid, wherein an oxidative agent comprising a chrom(VI)oxide derivative is used.

29. A liquid crystal display, optical element polarizer, compensator, color filter, charge transport material, chemical sensor, optical storage media, nonlinear optic, decorative pigment, adhesive, or synthetic resin, with anisotropic mechanical properties, comprising a liquid crystalline compound according to claim 13.

30. A liquid crystal display, optical element polarizer, compensator, color filter, charge transport material, chemical sensor, optical storage media, nonlinear optic, decorative pigment, adhesive, or synthetic resin, with anisotropic mechanical properties, comprising a liquid crystalline compound according to claim 18.

31. A liquid crystal display, optical element polarizer, compensator, color filter, charge transport material, chemical sensor, optical storage media, nonlinear optic, decorative pigment, adhesive, or synthetic resin, with anisotropic mechanical properties, comprising a liquid crystalline compound according to claim 15.

* * * * *